(12) United States Patent
You et al.

(10) Patent No.: US 9,089,288 B2
(45) Date of Patent: Jul. 28, 2015

(54) APPARATUS AND METHOD FOR NON-INVASIVE DIABETIC RETINOPATHY DETECTION AND MONITORING

(75) Inventors: Jia You, Hong Kong (CN); Qin Li, Hong Kong (CN); Zhenhua Guo, Hong Kong (CN); Qiang Sun, Hong Kong (CN); Chun Li, Hong Kong (CN)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 134 days.

(21) Appl. No.: 13/436,991

(22) Filed: Apr. 1, 2012

(65) Prior Publication Data

US 2012/0249959 A1 Oct. 4, 2012

Related U.S. Application Data

(60) Provisional application No. 61/469,824, filed on Mar. 31, 2011.

(51) Int. Cl.
| | |
|---|---|
| G06K 9/00 | (2006.01) |
| A61B 3/12 | (2006.01) |
| G06K 9/46 | (2006.01) |
| G06T 7/00 | (2006.01) |
| G06K 9/36 | (2006.01) |

(52) U.S. Cl.
CPC .............. *A61B 3/12* (2013.01); *G06K 9/0061* (2013.01); *G06K 9/00597* (2013.01); *G06K 9/36* (2013.01); *G06K 9/46* (2013.01); *G06K 9/4609* (2013.01); *G06K 9/4652* (2013.01); *G06T 7/0079* (2013.01); *G06T 7/0081* (2013.01)

(58) Field of Classification Search
USPC ......... 382/100, 115, 117, 128, 164, 165, 173, 382/181, 190, 203, 209, 215–218, 275
See application file for complete search history.

(56) References Cited

U.S. PATENT DOCUMENTS

| | | | | |
|---|---|---|---|---|
| 6,053,865 | A * | 4/2000 | Sugiyama et al. | 600/300 |
| 2004/0258285 | A1* | 12/2004 | Hansen et al. | 382/128 |
| 2010/0220906 | A1* | 9/2010 | Abramoff et al. | 382/130 |
| 2010/0238404 | A1* | 9/2010 | Newman et al. | 351/208 |

OTHER PUBLICATIONS

Qin Li, Xue-Min Jin, Quan-xue Gao, Jane You, and Prabir Bhattacharya, "Screening Diabetic Retinopathy Through Color Retinal Images", Medical Biometrics, First International Conference Proceedings, ICMB, Jan. 2008, pp. 176-183.*

(Continued)

*Primary Examiner* — Eric Rush
(74) *Attorney, Agent, or Firm* — Duane Morris LLP; Siegfried J. W. Ruppert

(57) ABSTRACT

A fundus camera using infrared light sources, which included an imaging optical path and an optical path for focusing and positioning and two optical paths share a common set of retina objective lens, and a computer-assisted method for retinal vessel segmentation in general and diabetic retinopathy (DR) image segmentation in particular. The method is primarily based on Multiscale Production of the Matched Filter (MPMF) scheme, which together the fundus camera, is useful for non-invasive diabetic retinopathy detection and monitoring.

13 Claims, 33 Drawing Sheets

(56) References Cited

OTHER PUBLICATIONS

Harihar Narasimha-Iyer, Ali Can, Badrinath Roysam, Charles V. Stewart, Howard L. Tanebaum, Anna Majerovics, and Hanumant Singh, "Robust Detection and Classification of Longitudinal Changes in Color Retinal Fundus Images for Monitoring Diabetic Retinopathy", IEEE, Transactions on Biomedical Engineering, vol. 53, No. 6, Jun. 2006, pp. 1084-1098.*

Chanjira Sinthanayothin, James F. Boyce, Helen L. Cook, and Thomas H. Williamson, "Automated Localisation of the Optic Disc, Fovea, and Retinal Blood Vessels from Digital Colour Fundus Images", British Journal of Ophthalmology, vol. 83, Issue 8, 1999, pp. 902-910.*

Herbert F. Jelinek, Michael J. Cree, Jorge J. G. Leandro, Joao V. B. Soares, Roberto M. Cesar, Jr. and A. Luckie, "Automated Segmentation of Retinal Blood Vessels and Identification of Proliferative Diabetic Retinopathy", Optical Society of America, vol. 24, No. 5, May 2007, pp. 1448-1456.*

Anantha Vidya Sagar, S. Balasubramaniam and V. Chandrasekaran,"A Novel Integrated Approach using Dynamic Thresholding and Edge Detection (IDTED) for Automatic Detection of Exudates in Digital Fundus Retinal Images", IEEE, Proceedings of the International Conference on Computing: Theory and Applications, 2007, pp. 705-710.*

Abramoff, M.D., et al., "Evaluation of a system for automatic detection of diabetic retinopathy from color fundus photographs in a large population of patients with diabetes," *Diabetes Care*, vol. 31, No. 2, pp. 193-198 (2008).

Faust, O., et al., "Algorithms for the automated detection of diabetic retinopathy using digital fundus images: a review," *J Med Syst*, vol. 36, pp. 145-157 (2012).

Heikkilä, M., et al., "A texture-based method for modeling the background and detecting moving objects," *IEEE Transactions on Pattern Analysis and Machine Intelligence*, vol. 28, No. 4, pp. 657-662 (2006).

Hoover, A, et al., "Locating blood vessels in retinal images by piecewise threshold probing of a matched filter response," *IEEE Trans. Med. Imag.*, vol. 19, No. 3, pp. 203-210 (2000).

Kirbas, C., et al., "A review of vessel extraction techniques and algorithms," *ACM Comput. Surv.*, vol. 36, No. 2, pp. 81-121 (2004).

Ojala, T., et al., "A comparative study of texture measures with classification based on feature distributions," *Pattern Recognition*, vol. 29, No. 1, pp. 51-59 (1996).

Ojala, T., et al., "Multiresolution gray-scale and rotation invariant texture classification with Local Binary Pattern," *IEEE Trans. Pattern Analysis and Machine Intelligence*, vol. 24, No. 7, pp. 971-987 (2002).

Spencer, T., et al., "An image processing strategy for the segmentation and quantification of microaneurysms in fluorescein angiograms of the ocular fundus," *Computers in Biomedical Research*, vol. 29, pp. 284-302 (1996).

* cited by examiner (a)

(b)

(a)

(b)

(a)      (b)      (c)
(d)      (e)      (f)

(a)      (b)      (c)
(d)      (e)      (f)

(a)

(b-1)

(b-2)

(c-1)

(c-2)

(d-1)

(d-2)

(a)                      (b)

(a)

(a)

(b)

(c)

(d)

(a)  (b)
(e)  (f)

(a)  (b)

(a)  (b)

(a)

(b)  (c)

(a)

(d)

(b)

(e)

(c)

(f)

(a)

(b)

(a)

(b)

(c)

(a)

(b)        (c)

APPARATUS AND METHOD FOR NON-INVASIVE DIABETIC RETINOPATHY DETECTION AND MONITORING

CROSS REFERENCE OF RELATED APPLICATION

This application claims benefit from U.S. Provisional Application No. 61/469,824, filed Mar. 31, 2011, the content of which is incorporated herewith by reference in its entirety.

FIELD OF THE INVENTION

This invention relates to a computer-assisted technology for diseases diagnosis. Particularly, it relates to a computer-assisted apparatus and method for non-invasive diabetic retinopathy detection and monitoring.

BACKGROUND OF THE INVENTION

The human retina offers a window into the health of a person. Retinal microvasculature is the only part of the human circulation that can be visualized non-invasively in vivo, readily photographed and quantitatively analyzed. The content of a retinal image with high resolution structure of photoreceptors and vascular flow offers detailed information that would enable doctors to make early and accurate diagnosis of diseases. Clinical signs discernible in retinal fundus images include microaneurysms, dot and blot hemorrhages, exudates and intra-retinal micro-vascular abnormalities. Such retinal disorders impose serious attacks to the eye which may lead to the loss of vision or even blindness. Some retinal diseases are even indications of systemic diseases such as diabetes, hypertension and arteriosclerosis. For example, Diabetic Retinopathy (DR) is a common complication of diabetes that damages the eye's retina. Therefore, the early diagnosis of vision threatening retinal diseases is important to the timely treatment to minimize further damages and deterioration.

Clinical signs used by medical specialists to diagnose retinal diseases are based on the examination of delicate structure of retina and its changes. Retinal imaging which combines computing and electronic imaging has emerged as an innovative technology to be used in large-scale screening programs with significant resource savings, free from observer bias and reliable aid in clinical decision-making. However, automated retinal image analysis is complicated by the fact that retinal features can vary from large vessels to tiny dots, and that the local contrast of retinal structure is unstable, especially in unhealthy ocular fundus. In addition, it is very time consuming to examine a large number of feature segments in retinal images. The success of a retinal imaging system depends on four key issues: 1) quality of retinal images (data acquisition), 2) effectiveness of retinal feature extraction and representation, 3) accuracy and efficiency to identify retinal abnormalities (mass screening and diagnosis) and 4) reliability to detect and classify changes in time series of retinal images (monitoring of the disease over time). It is a challenging task to develop a high performance retinal imaging system for computer aided medical diagnosis and monitoring with respect to robustness, accuracy, efficiency, safety and cost. The following is the fundamental issues existing in the art:

(a) Image Acquisition: how to capture good quality retinal images with flexibility and at low cost?

(b) Image Representation: how to extract multiple retinal features in different spectrum?

(c) Diagnosis/Screening: how to identify changes of retinal feature structures within individual image samples?

(d) Monitoring: Has any change occurred over a time series of retinal images?

SUMMARY OF THE INVENTION

Accordingly, one object of the present invention is to provide solutions to the aforementioned issues. This object is realized by providing a unique and special design of a new lighting and position alignment structure for fundus camera (hardware component) and a hierarchical retinal image analysis with new algorithms for multispectral image representation of the retina, dynamic feature extraction, reliable image registration, dynamic image tracking, hierarchical image matching and robust identification of changes (software component).

The above object is realized by two novel segmentation techniques. The first scale production is an efficient strategy for fusing multiscale vessel responses by identifying vessel pixels in the scale production domain. This scale production method makes it possible to enhance vessels while suppressing noise because the vessels will have relatively strong responses to the matched filters along scale space while the background noise decreases rapidly. As a result, the method can extract both wide and thin vessels concurrently with low computational complexity.

The second technique is a modified matched filter approach, which detects vessels in a retinal image while suppressing non-vessel edge structures. The modified matched filter does not remove the image background but uses a local double-side thresholding to avoid responding to non-line edges. As a result, the method does a good job of detecting the neovasculars and eliminating many non-vessel edges caused by bright lesions. This is a desirable property in PDR (proliferative diabetic retinopathy) screening because the edges of bright lesions have large curvatures which make them easy to misclassify as neovasculars.

The object of the present invention is further achieved by a novel system for segmenting the main regions and lesions of colour retinal images obtained from patients with diabetic retinopathy (DR). The system can be used to extract major features of the retina for use in the diagnosis of diabetic retinopathy. The system shows a satisfactory accuracy for DR screening in large populations and offers two main advantages. First, it can suppress the interaction among features during the process of feature extraction. Second, it is efficient because it extracts all features in a single flow, which allows the use of earlier extracted features such as bright lesions and red lesions in the extraction of features later in the flow such as vessels, optic disks, and foveae.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DESCRIPTION OF PARTICULAR EMBODIMENTS OF THE INVENTION

Hardware Aspect

Although recent advances in optical instrumentation such as adaptive optics (AO), scanning laser ophthalmoscopy (SLO), optical coherence tomography (OCT) and non-mydriatic retinal cameras provide high resolution photos of retinal structure, the conventional ophthalmology-based method is time consuming because it requires extraction of lots of ophthalmological parameters, such as visual acuity, shape and size of optic disc, status of the anterior segment and fundus, thickness of vessels, and the distribution of retinal nerves by the ophthalmologist manually for decision making in diagnosis. Fundus camera has been adopted by ophthalmologists as one of the commonly used medical device to capture retinal images for clinical examination and analysis. It plays an important role for the quality of images. The first fundus camera in the world was developed by German company CAR ZEISS in 1925. The optical design and system structure have been improved significantly as the result of market demand and competition among many medical device manufacturers in Japan, USA, Germany during the past years. The well known models are made by Cannon, Topcon, Opton, Nikon, Olympus, Visual Path and Nidek etc. Although the individual design of lighting component varies among different models, the system structure is similar, which consists of three components for lighting, observation and imaging. With the advances in optical and digital sensor technologies, new fundus cameras have been developed with good quality of images, compact system structure, real-time digital data acquisition and preprocessing. Nonetheless, the existing models of fundus camera have issues: (a) they are expensive and (b) they offer only simple preprocessing functions for retinal image acquisition and storage. The fundus camera according the present invention meets the needs for high performance, good quality of images, low cost and advanced capacity for comprehensive data analysis. The new fundus camera comprises the following technical features:

(a) A new lighting design with the infrared light source to minimize the disturbance to retina caused by the change of light intensity;

(b) The use of three-colour PD lighting tubes for the generation of colour retinal image;

(c) The dynamic control of eye position alignment to ensure system reliability;

(d) The automatic control of lighting, sampling and storage by special software.

Particular Embodiments of a Fundus Camera According to the Present Invention

Figure 1A:
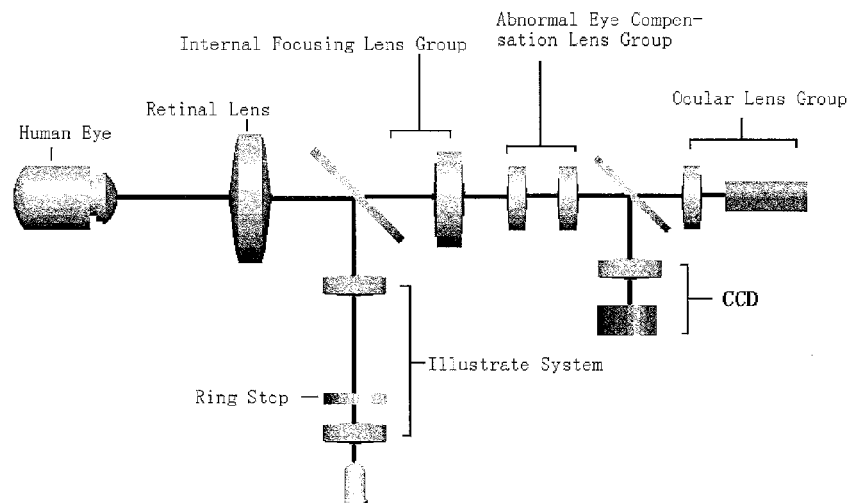
FIG. 1A shows the structure and optical paths of an fundus camera of the present invention.

As shown in FIG. 1A, an embodiment of the fundus camera of present invention consists of six components: object lens group, lighting system (illustration), internal focus lens group, abnormal eye compensation lens group, ocular lens group and CCD. The function of each component is listed as follows:

1) object lens group: special group of lenses to capture retinal image; 2) lighting: lighting source for uniformed lighting in fundus area; 3) internal focus lens group: lens adjustment for robust image acquisition; 4) abnormal eye compensation lens group: adjustment to compensate the abnormal eye condition (−20D-20D) in fundus area −20D-20D compensation; 5) ocular lens group: direct observation of objects; and 6) CCD: capturing images by CCD.

Figure 1B:
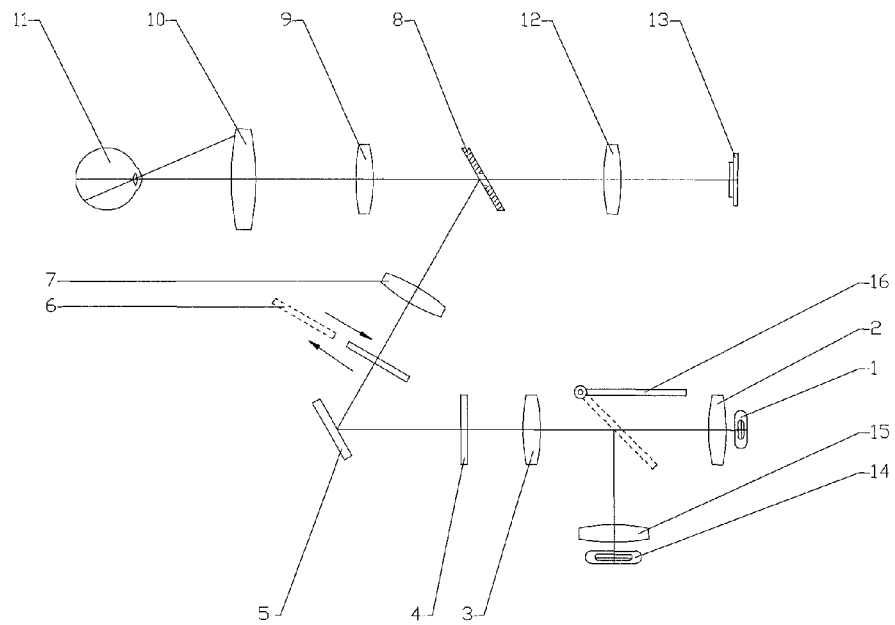
FIG. 1B shows the structure and optical paths of another fundus camera of the present invention.

FIG. 1B shows another embodiment of the fundus camera. It achieves a high precision and clear imaging of the retina. It can take the retinal image from a 45 degree view field angle and achieve focus compensation for abnormal human eyes from 2000 degrees of myopia to 2000 degrees of hyperopia. The camera comprises an imaging optical path and an optical path for focus positioning. The optical path for focus positioning is for lighting on the fundus and producing positioning signals and the imaging signals. It comprises retina objective lens 10, zoom lens group 9, relay lens 7, target cross-hair plate 6, annular aperture 4, condensers 3, 2, 15, and near-infrared light sources 1, 14. The imaging optical path comprises retina objective lens 10, zoom lens group 9, imaging lens 12, and imaging CCD 13 (charge-coupled device, i.e., digital camera). This is a camera of coaxial optical path, where the imaging optical path and the optical path for focusing and positioning share a common set of retinal lens.

In order to achieve fast and clear imaging, the entire process makes full use of near-infrared light for focusing, positioning, and shooting. Considering variations of human eyes, an reflective mirror 8 is added to the path which can vary its aperture size to ensure the consistency of the amount of CCD exposure. Before completion of the fundus imaging, the CCD first detects the light energy from the fundus and, based on the amount of the energy, it automatically selects an aperture size of reflective mirror 8 to control the sensor's exposure to the light ensure that the fundus is consistently illuminated. Finally, the camera system uses a zoom lens 9, which is positioned behind retina objective lens 10. By moving the zoom lens, both the imaging optical path and positioning optical path changes their focal length. In this manner, changing only one zoom lens in the camera system can achieve focal length compensation for non-normal eyes, greatly simplifying the mechanical structure to reduce the equipment size and improve the alignment accuracy when setting up the instrument.

The operating process can be divided into two steps. The first step is to focus and position and the second step is to shooting.

Focusing and Positioning Process: A continuous light source 1 provides continuous illumination for focusing and positioning. The positioning light first passes through the condenser, 2, 3, forms the source image at position 4, and after being reflected by mirror 5 produces a uniform illumination surface at position 6. Position 4 and the pupil plane conjugate and position 6 and the retina conjugate. An annular aperture is placed on the source image plane at position 4 and a target plate with a cross-hair is placed on the uniform illumination surface at position 6. After passing replay mirror 7 and reflector 8, the optical path for focusing and positioning joins the optical path for imaging to achieve the co-axial illumination, that is, both the optical paths share a common set of retina lens. The positioning beam passes through focusing lens group 9 and retina objective lens 10 to reach the pupil. The annular aperture at this location produces a clear image and the use of the ring-shaped aperture ensures that the incident illumination beam enters the eye from the peripheral of the pupil, avoiding corneal reflected light from entering into the imaging optical path, and thus increasing the contrast of the image. The light entering the eye illuminates the retina and projecting out a cross-hair targeting symbol. Part of the light energy is absorbed by the retina, and another part of the light energy is reflected into the imaging light path as optical signals. The optical signals come out of the pupil and pass through objective lens 10, zoom lens group 9, hollow reflective mirror 8, the imaging lens 12 and reaches CCD 13. At this point, the cross-hair symbol can be observed on the CCD. Adjusting the zoom lens group to ensure imaging clarity on the CCD based on the cross-hair symbol and now the focusing and positioning process is complete.

Shooting Process: Light source 14 is used as shooting flash, and it will produce high-brightness illumination. After the above described focusing and positioning process is complete, click the "shooting" button, light source 14 will produce flash pulse. Before the flash pulse is generated, the system performs the following operations: reflection plate 16 is down, the cross-hair target plate is out of the optical path, the CCD starts to capture the image. Then comes the flash. The flash beam passes through condenser 15 and reflection plate 16 and enters into the optical path for focusing and positioning where it passes through condenser 3, annular aperture 4, reflective mirror 5, relay mirror 8, hollow mirror 7, zoom lens group 9, and retina objective lens 10 and enters into the eye. The retina reflects part of the beam and turns it into optical signals, which then pass through retina objective lens 10, focusing lens group 9, hollow mirror 7, and imaging lens 12, and then form retinal image on CCD 13. This completes the capture process.

Software Aspect

According to the present invention, hierarchical retinal image analysis is designed for automated medical diagnosis and monitoring. The software aspect of hierarchical retinal image analysis can be decomposed into a number of related components to address the key issues—feature extraction, vessel segmentation, change detection and classification, respectively. These tasks, the techniques that will be used to solve them, and the relevant computing algorithms that will be used to implement the tasks are described below.

Establishment of a Multi-Scale Analytical Scheme for Multiple Feature

This mainly concerns with the extraction of multiple retinal image features at different scales based on Gabor filters and scale production.

Multiple Feature Extraction—Feature Points, Lines, Ridges and Texture. Edge detection is regarded as an essential early step in most scene analysis systems. However, the use of edges as image features is limited because simple edge detectors are susceptible to noise and a large portion of output edge points are redundant. Inventors' previous work, however, demonstrated that combining Gabor filter with Plessey operator is able to extract interest points as retinal image feature points at different scales.

Traditional line detection methods proceed either by finding parallel edges or by finding ridges. Unfortunately, these algorithms detect lines based on a single optimal value of filter scale and are not powerful to detect vessels of various size at different scales. In the present invention, a novel approach is developed to overcome the limitations. This approached will be further described below.

Texture is an essential element in segmenting images and interpreting scenes. However, most of the research on retinal image analysis are concerned with detection of edges, lines and ridges. In the present invention, we introduce the texture concept to describe the distribution of retinal vessels and apply the so called 'spatial-statistical' measurement for feature representation.

Multiscale Scheme—Gabor Filtering and Scale Multiplication

This concerns handling multiple features at different scales. The research finding reported by Mallat shows that signals and noise have different singularities and that edge structures present observable magnitudes along the scales, while noise decreases rapidly. Based on this observation, we extend our previous work on scale multiplication and develop a new multiscale analytical scheme by combining Gabor filtering with scale production to achieve high performance in edge detection and noise reduction. We modify the Gabor filter equation by adding a scale parameter to control the filter size, which is expressed as follows:

$$g_{\phi,s}(x,y) = \exp\left\{-\pi\left(\frac{x'^2}{(s\sigma_x)^2} + \frac{y'^2}{(s\sigma_y)^2}\right)\right\}\cos(2\pi f x')$$

The response of Gabor filter is expressed by $R_g(x,y) = g_{\phi,s}(x,y) * f(x,y)$, where $f(x,y)$ is the image and $*$ is convolution. The scale multiplication is defined as the product of Gabor filter responses at two adjacent scales $P^{s_j}(x,y) = R_g^{s_j}(x,y) \cdot R_g^{s_{j+1}}(x,y)$. In addition, a tuning process to optimize the selection of scale parameters may be applied.

Development of a Hierarchical Structure for Red Lesion Detection and Bright Lesion Analysis in Retinal Images This primarily concerns with the extraction of retinal vessel features at different scales for the detection of red/bright lesions by multiscale correlation filtering and controlled morphological reconstruction.

Figure 2A:
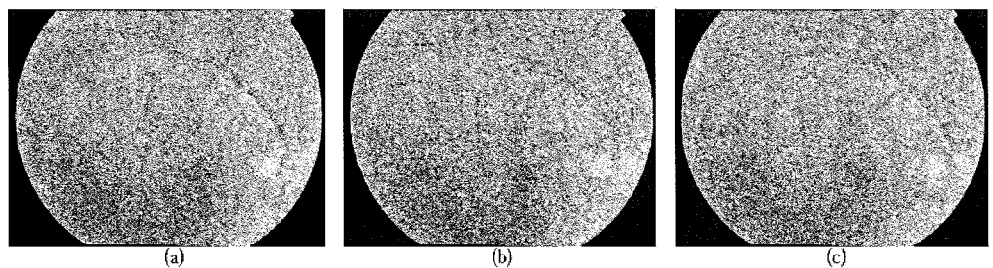
FIG. 2A is an illustration of hierarchical detection, (a) marked (square) sample retinal image, (b) candidates after coarse level detection, and (c) fine level classification.

Retinal red lesion detection by multiscale correlation filtering is an image-based approach to hierarchical detection of red lesions for computer aided diagnosis of DR. The detection and classification of red lesions is difficult due to the complicated background and illumination variances in retinal images. To tackle these problems, the present invention combines a multiscale correlation frame with a dynamic thresholding scheme for intensity-based detection and localization of red lesions in retinal images. According to the present invention, the method includes: 1) Coarse Level Red Lesion Candidate Detection based on Multiscale Correlation Filtering; 2) Fine Level: True Red Lesion Detection. The effectiveness and feasibility of this approach to red lesion detection is demonstrated in FIG. 2A, where (a) shows the original input image for testing, (b) is the output at coarse level and (c) shows the final marked lesion point after fine-level classification. The operating process of this hierarchical scheme is further described as follows.

Coarse Level: Red Lesion Candidate Detection based on Multiscale Correlation Filtering. Cross-correlation is widely used for intensity-based object localization. Although the inner-product score is effective for matching, the exhaustive search for matching object models is inefficient in two dimensions and becomes infeasible in higher dimensioned configuration spaces with multiple features. The Bayesian framework for correlation is developed to replace exhaustive search with constrained, random hypothesis generation. The Bayesian correlation algorithm consists of three components to establish cross-correlation measurement with probabilistic sampling: 1) generation of observation likelihood to interpret correlation matching functions in probabilistic terms, 2) a response-learning procedure for image-feature tuning throughout filter-bank outputs, 3) layered sampling for multiscale operation. The advantages of Bayesian correlation are characterized by its simple estimation of location and robust handling of image clutter.

As the size of red lesions is very small and the traditional edge-based methods for object localization are not suitable to detect red lesions accurately. In the present invention, Bayesian correlation filtering is extended by applying Gaussian-shaped filter-bank at different scales to capture foreground/background transitions based on the probabilistic model of intensity correlation. In addition, a feature-based tuning procedure is developed for filter response-learning, which includes background likelihood learning and foreground likelihood learning. Moreover, layered sampling is applied to reduce computation complexity of factored sampling caused by the narrow observation likelihood function, where filter responses at different scales are used simultaneously. In the present invention, the effectiveness of multiscale correlation filtering for the detection of small sized red lesions in retinal images subject to various disturbances is demonstrated by its robustness of variance reduction and occlusion handling. When the responses of the correlation filtering are larger than a threshold, the spots are regarded as the candidates of the red lesions.

Fine Level: True Red Lesion Classification. The fine level lesion detection is to detect true red lesions in the candidate set, which can be implemented through feature extraction. At this level, false red lesions from the candidates detected previously at coarse level are removed. Since red lesions do not occur on vessels, an adaptive thresholding scheme is applied as follows: Firstly, the vessels are extracted and the candidates of red lesion which are connected to the vessels are removed. Secondly, for each remaining candidate, a feature-based region growing algorithm is applied. Finally, features based on shape, grayscale/colour pixel intensity, responses of Gaussian filter-banks and correlation coefficient values are extracted for each candidate. As many as 31 features may be used for each candidate, based on shape, grayscale pixel intensity, color intensity, responses of Gaussian filter-banks, and correlation coefficient values. The minimum and maximum values of each feature for all true lesions are placed in a discrimination table. This is used to remove any candidates whose features are below the minimum or greater than the maximum defined in the discrimination table. Candidates left behind after this stage are classified as true red lesions.

Bright Lesion Analysis by Controlled Morphological Reconstruction

Figure 2B:
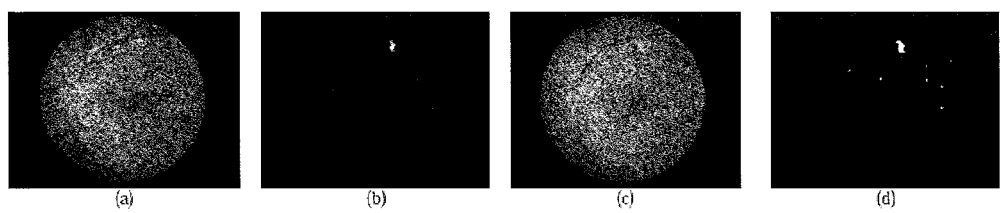
FIG. 2B shows the way of finding contour of bright lesions according to the present invention. (a) Reconstructed image $I_5$, (b) Difference between $I_5$ and $I_g$ (c) Optic nerve, (d) Bright Lesions.

This is to tackle the problem of bright lesion detection and classification by controlled morphological reconstruction in a hierarchical structure. According to the present invention, the method includes: 1) bright lesion detection through controlled morphological reconstruction; 2) coarse level classification based on size; and 3) fine level classification based on color and edge. After bright lesion detection, candidates can be classified to waxy exudates or cotton wool spots. Waxy exudates are hard and yellow; cotton wool spots are soft and white. A feature vector is formed by combing edge strength, size, and color of lesions. Then SVM (support vector machine) was used as classifier. However, the edge strength and color of small size bright lesions are very unstable. If all of these features are combined as a single feature vector, the discriminant ability of the classifier will be low. Since bright lesions with a too small size can not be cotton wool spots, two-level classification are used here. At the coarse level, too small bright lesions will be thresholded as waxy exudates. At the fine level, other bright lesions will be classified as waxy exudates or cotton wool spots. We use SVM classifier at the fine level classification. The optimal separating hyperplane given by SVM in the feature space is defined as $$f(x) = \text{sgn}\left(\sum_{i=1}^{c} y_i \alpha_i K(x_i, x) + b\right)$$

where $y_i$ are the labels for classes, $\alpha$ are the Lagrange multipliers, K is the kernel function, b is the bias, and x is the feature vector. The features are edge strength and color. FIG. 2B shows an exemplary performance of this approach to DR (diabetic retinopathy) diagnosis. In FIG. 2B, (a) is the reconstructed image $I_5$, (b) is the difference between $I_5$ and the green channel of original color image $I_g$, (c) is optic nerver, and (d) shows bright lesions.

Robust Change Detection and Classification for Diabetic Retinopathy Monitoring

This primarily concerns with the robust detection and classification of longitudinal changes in retinal images for diabetic retinopathy monitoring.

Tensor Based Feature Representation. This addresses the question of whether any change occurs in a time series of retinal images. Change analysis is an important research topic in various areas and there have been many algorithms developed for change detection in images. However, the performance of the direct use of the known algorithms to detect the changes in a time series of retinal images is not satisfactory because of the variations of illumination conditions and vessel sizes. In the present invention, a tensor based feature representation structure is developed to facilitate multiple feature extraction and representation for robust change detection. Firstly, the feature detector as described above is used to extract physiological and pathological features for each individual frame of the time series of retinal image series. These features are described by high dimensional vectors. Finally, the set of these high dimensional vectors are defined as a tensor to represent a time series of retinal images.

Tensor Discriminant Analysis. This is to optimize the output of change detection. We apply a general tensor discriminant analysis (GTDA) as a preprocessing step for LDA (Linear Discriminant Analysis). The benefits of GTDA compared with existing preprocessing methods, e.g., principal component analysis (PCA) and two-dimensional LDA (2DLDA), include 1) the under-sample problem (USP) is reduced in subsequent classification by, for example, LDA; 2) the discriminative information in the training tensors is preserved; and 3) GTDA outperforms 2DLDA by providing stable recognition rates because the alternating projection optimization algorithm to obtain a solution of GTDA converges. Combining GTDA with LDA, the data can be projected from the higher dimensional original space to a lower dimensional feature space. Then, the support vector regression (SVR) can be applied to reveal the relationship between the extracted features and the pathological patterns.

Segmentation of Retinal Vessels Using MPMF

Now turning to description of the retinal vessel segmentation using Multiscale Production of Matched Filters (MPMF) according to the present invention. Vessel segmentation is a specific line detection problem and hence many existing vessel extraction algorithms were originated from line detection techniques. In order to segment vessels, the first step usually is to enhance vessels. Vessel enhancement is usually implemented locally by using a window centered at the pixel to be enhanced. This class of techniques originated from the classical image processing problem: finding edges and lines in an image. For example, the matched filter was first proposed to detect retinal vessels. The matched filter is an effective technique for enhancing vessels by exploiting the prior information that the cross-section of the vasculature is Gaussian-shaped. However, the matched filter at a single scale cannot effectively enhance all the vessels of variant widths. Even when multiple filters with multiple scales are used, some small and weak vessels still cannot be detected due to the low density contrast and relatively heavy background noise.

The matched filter is based on the prior knowledge that the cross-section of a retinal vessel is Gaussian-shaped. Therefore a Gaussian-shaped filter can be used to "match" the vessel. If there exists a vessel and its width matches the scale of the filter, a strong response will appear and then the vessel can be detected. Another advantage of the Gaussian-shaped matched filter is that it can smooth noise. A single scale matched filter was reportedly used to detect vessels in the retinal image and the scale of the filter was determined by experience. The matched filter with a single scale, however, cannot produce strong responses to all vessels in the retinal image when the width variance is large.

Some multiscale schemes have been proposed for vessel detection. However, with the known multiscale schemes, some small and weak vessels still cannot be detected because they are not successfully enhanced at any of the multiple scales.

In the present invention, a new multiscale vessel extraction scheme is developed that uses Multiscale Production of the Matched Filter (MPMF) responses as the multiscale data fusion strategy. This MPMF vessel extraction scheme includes: (1) multiscale matched filtering and scale multiplication in the image enhancement step; and (2) double thresholding in the vessel classification step. Considering that the vessel structures will have relatively strong responses to the matched filters at different scales but the background noise will not, multiplying the responses of matched filters at several scales will further enhance the vessels while suppressing the noise. The vessel pixels can then be detected and fused in the scale production domain. This scale multiplication strategy has three advantages. One is that the vessels of variant widths can be detected concurrently because it can incorporate the multiscale information. Another is that it can detect the small and weak vessels which cannot be detected by other methods because the weak vessels could be better enhanced (while the noise being significantly suppressed) in the scale production domain. The third advantage of the proposed method over some snakes and tracking based classification methods is that it is much easier to implement and has much lower complexity.

The Multiscale Matched Filters Using Scale Production

This method is able to detect large and small vessels concurrently. It also offers an efficient way to suppress noise, making it possible to detect some small weak vessels with low local contrast.

Scale Production of the Multiscale Matched Filters

Figure 3:
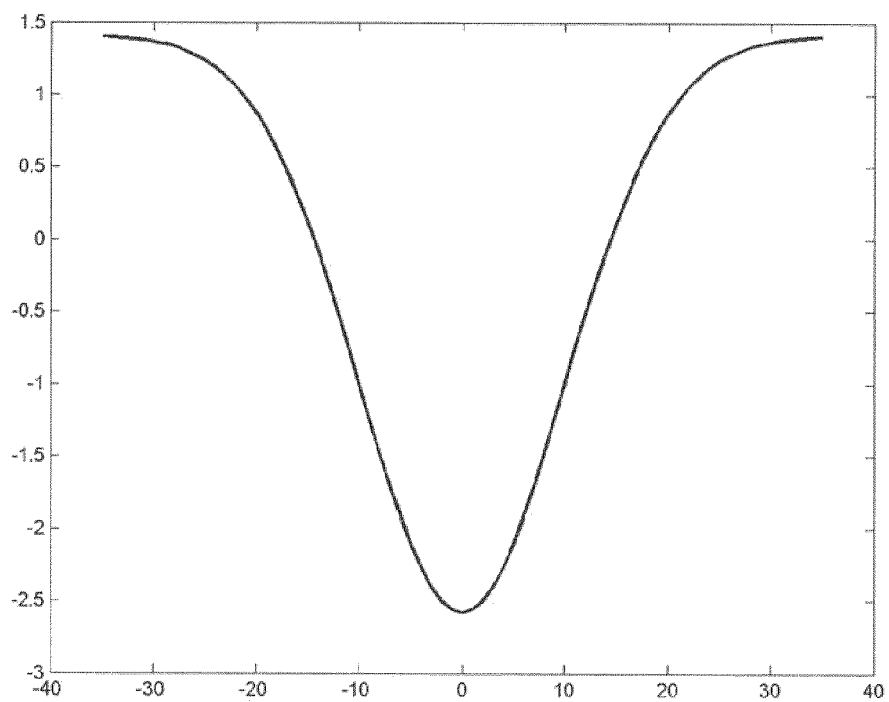
FIG. 3 shows plots of the 1-D cross section of a matched filter (a) and the 2-D matched filters at 3 different scales and in 8 directions (b).
Figure 3:
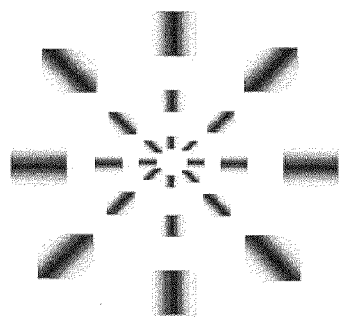

The effectiveness and efficiency of matched filters is known previously and the retinal vessels are enhanced and extracted from noisy background using a single filter at a single scale. The matched filter is adopted in the multiscale scheme of the present invention because it well exploits the prior knowledge that the cross-section of a retinal vessel is Gaussian-shaped. We re-write the function of the matched filter defined previously from $g(x,y) = -\exp(-x^2/\sigma^2) - m$, for $|x| \leq 3\sigma$, $|y| \leq L/2$ to:

$$g_i(x,y) = -\exp(-x^2/\sigma_i^2) - m_i, \text{ for } |y| \leq L_i/2$$

where $\sigma_i$ is the standard deviation of the Gaussian function at scale i. Correspondingly, $m_i = -(\int_{-3\sigma_i}^{3\sigma_i} \exp(-x^2/\sigma_i^2)dx)/(6\sigma_i)$, and $L_i$ is the length of the filter in y direction at that scale. The rotation of $g_i(x,y)$ with angle $\phi$ is then implemented by using $g_i^\phi(x',y') = g_i(x,y)$, where $x' = x \cos \phi + y \sin \phi$ and $y' = y \cos \phi - x \sin \phi$. FIG. 3 (a) plots the 1D cross section of a matched filter and FIG. 3 (b) shows the 2D matched filters at 3 different scales and in 8 directions.

Without loss of generality and for the convenience of expression, we only discuss the multiscale matched filter in the horizontal direction. The filters in other directions can be derived similarly. The response of a matched filter $g_i(x,y)$ to an input image $f(x,y)$ can be expressed by $$R_i(x,y) = g_i(x,y) * f(x,y) \quad (3.4)$$

The scale production is defined as the product of filter responses at two different scales $$P_{i,j}(x,y) = R_i(x,y) \cdot R_j(x,y) \quad (3.5)$$

Figure 4:
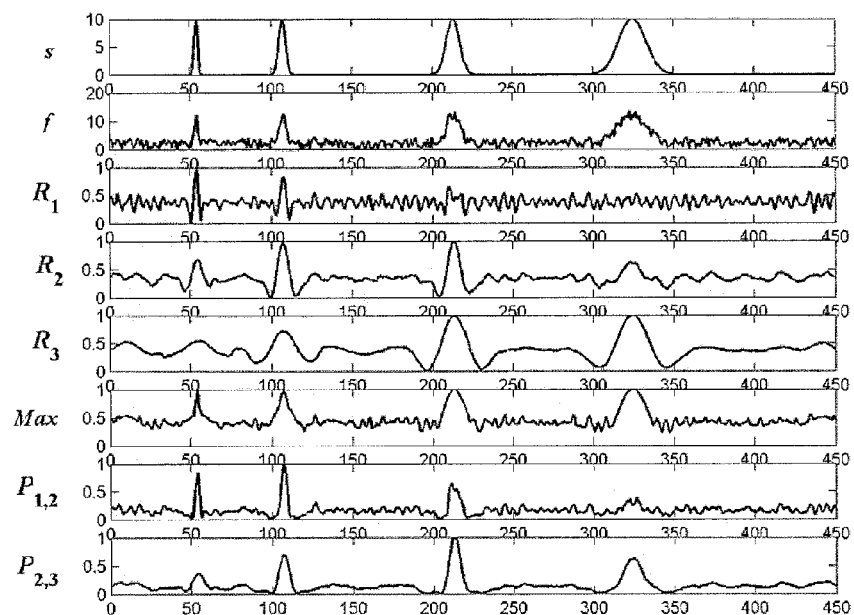
FIG. 4 illustrates multiscale matched filters and scale production. s is the original signal; f is the noisy measurement of s; R1, R2 and R3 are the matched filter responses to f at different scales. Max means the maximum values among R1, R2 and R3. P1,2 is the scale production of R1 and R2, and P2,3 is the scale production of R2 and R3.

Referring to FIG. 4, examples of the scale multiplication of the matched filters are shown. $P_{1,2}$ is the production of the filter responses at scales 1 and 2, while $P_{2,3}$ is the production of the filter responses at scales 2 and 3. Obviously, the filter responses to vessels of all widths can be better enhanced in $P_{1,2}$ and $P_{2,3}$ than in $R_1$, $R_2$ and $R_3$. The noise is also better suppressed in $P_{1,2}$ and $P_{2,3}$. The width of thin vessels will be enlarged by large scale filters, such as $g_2$ and $g_3$. Interestingly, this distortion could be corrected to some extent by employing a smaller scale filter in the scale production, as we can see in $P_{1,2}$. Finally, the vessels of variant widths and noise can be more easily discriminated in the scale production than in the original filter responses by using a simple thresholding strategy.

Based on the above observation and discussion, in the multiscale matched filters of the present invention, the production $P_{1,2}$ is used to extract small, thin vessels and the production $P_{2,3}$ is used to extract big, wide vessels after thresholding. We will then get two binary vessels maps and they are directly fused by using an "OR" logic operation to yield the final vessel map. Two key elements in the scheme of the present invention are multiscale selection and thresholding.

Multiscale Selection

In the multiscale matched filter scheme according to the present invention, three filters at three scales (small, middle, and big) are employed and hence two scale productions are computed. The selection of scales is very important. In the case of retinal images, the widths of vessels vary from 3 to 15 pixels (STARE and DRIVE databases). To determine the reasonable scales of the three filters, the following experiment were designed.

Figure 5:
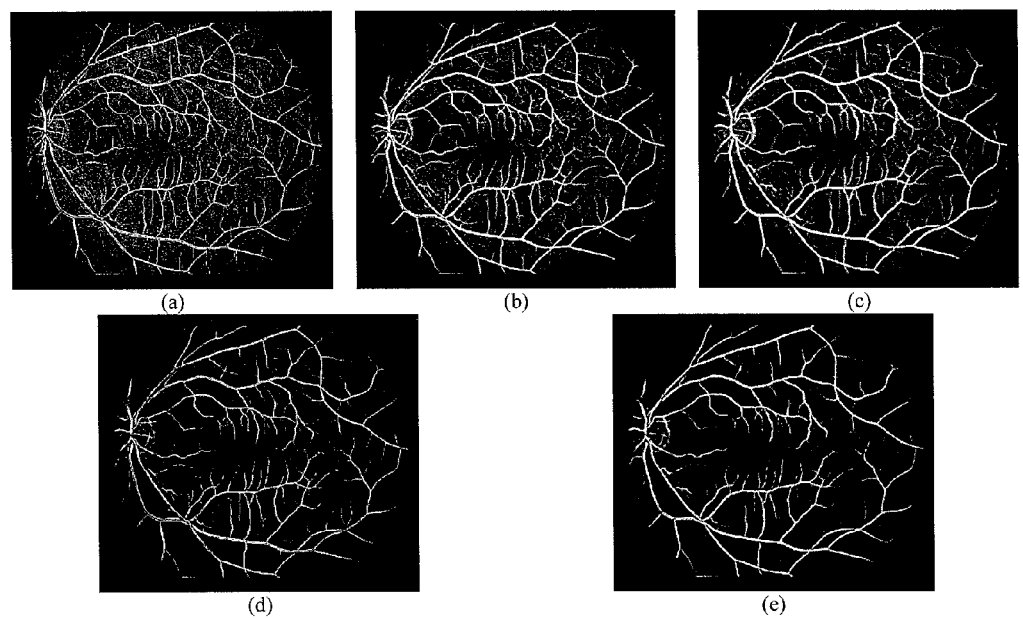
FIG. 5 illustrates multiscale filtering of a retinal image. (a), (b), and (c) are the matched filter responses to the retinal image at three scales; (d) is the scale production of (a) and (b); (e) is the scale production of (b) and (c).
Figure 6:
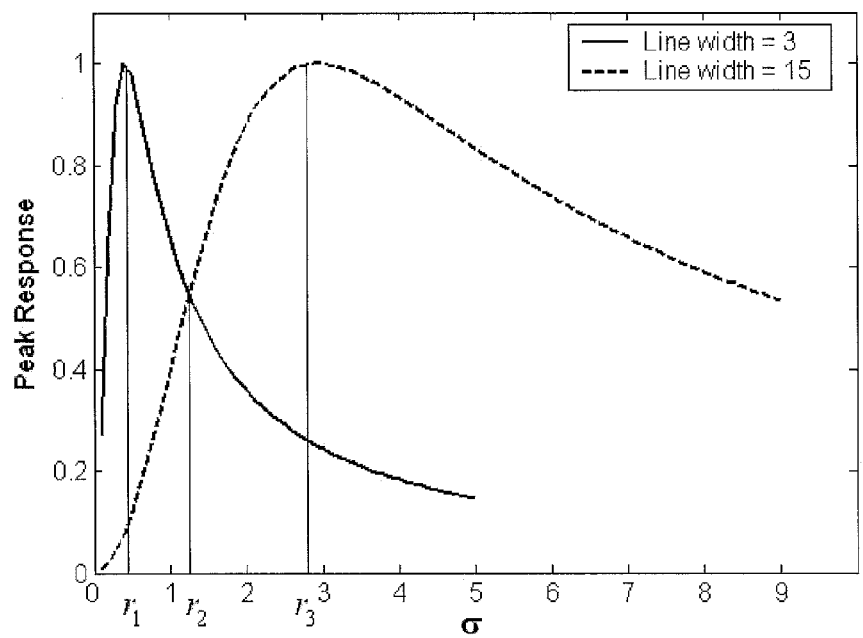
FIG. 6 shows filter peak responses to the thinnest and widest vessels along scale space.
Figure 7:
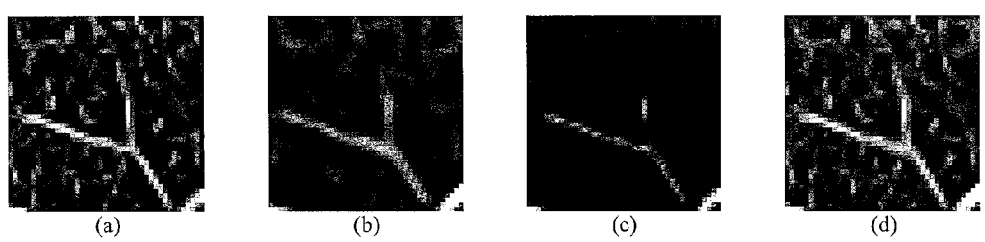
FIG. 7 shows cropped and enlarged images (a) and (b) from FIGS. 6 (a) and (b), respectively; (c) is the scale production of (a) and (b); (d) is the maximum of all the three scales (a), (b) and (c) in FIG. 6.
Figure 8:
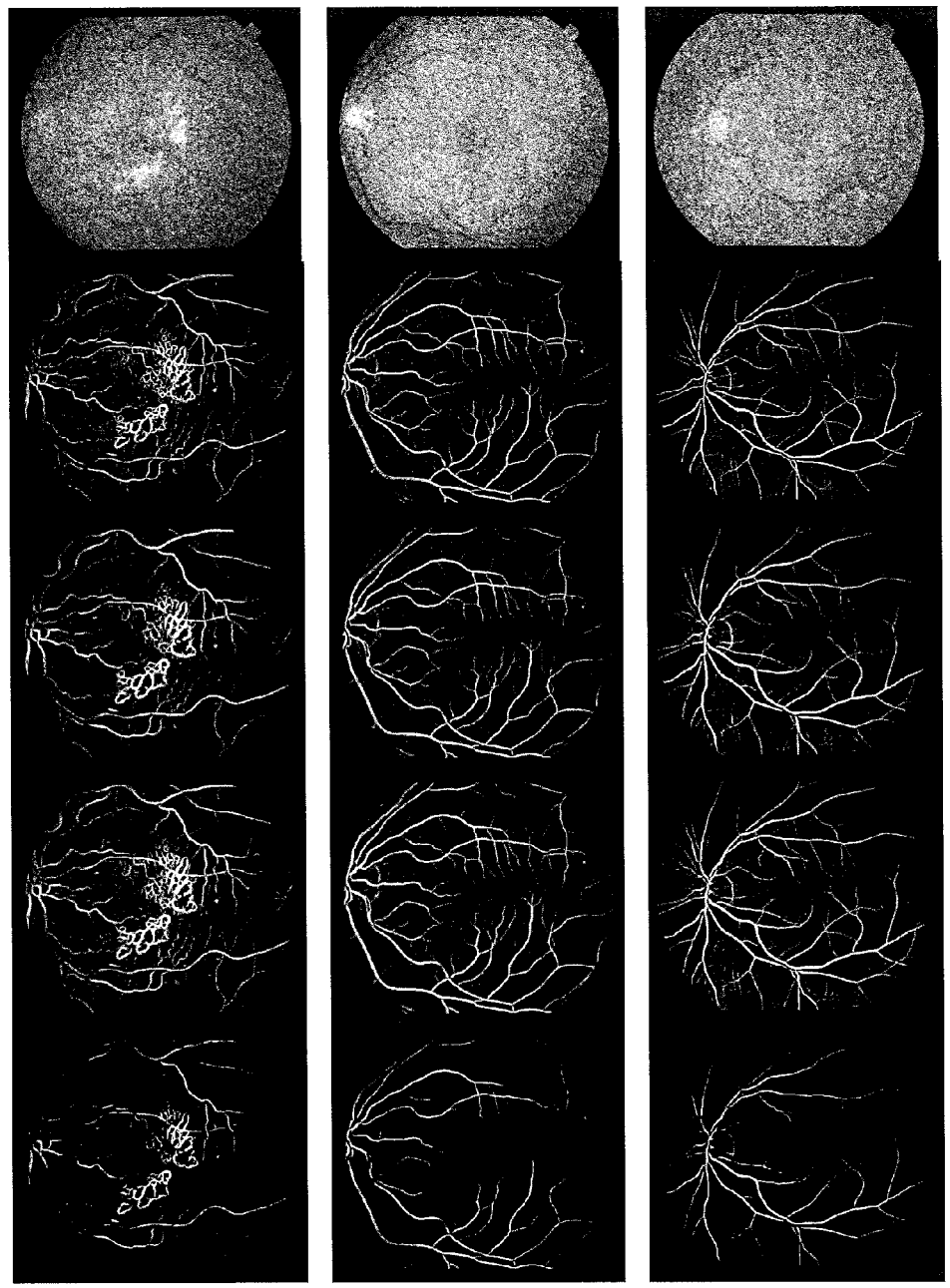
FIG. 8 shows the fusion of multiscale line responses. First row is the original images. Second row and third row are line responses at different scale. Fourth row is the maximum of multiscale line responses. The last row is the scale products of multiscale line responses.

The scale of the filter was varied from 0 to 9 and applied to the two types of vessels in the retinal image: the thinnest vessel (3 pixels wide) and the widest vessel (15 pixels wide). The curves of the peak responses of the filters to the two vessels versus the scales of the filters are plotted in FIG. 5. As shown there, the matched filer $g_i$ gets the highest response to the thin vessel if its scale parameter is set as $\sigma_i = r_1 (0.4)$. On the other hand $g_i$ will get the highest response to the wide vessel if its scale parameter is set as $\sigma_i = r_3 (2.7)$. The two curves cross at $\sigma_i = r_2 (1.3)$. Guided by FIG. 6, the scales of the three matched filters is set as $\sigma_1 = r_1$, $\sigma_2 = r_2$ and $\sigma_3 = r_3$, respectively and the three corresponding filters are denoted as $g_1$, $g_2$ and $g_3$. We detect the small, thin vessels in the scale production $P_{1,2}$ of the responses of $g_1$ and $g_2$, and detect big, wide vessels in the scale production $P_{2,3}$ of the responses of $g_2$ and $g_3$. FIG. 5 shows an example of a multiscale filtering scheme of the present invention, where (a)~(c) are the filter responses $R_1$, $R_2$, and $R_3$ at scales $\sigma_1 = r_1$, $\sigma_2 = r_2$ and $\sigma_3 = r_3$, (d) is the scale production $P_{1,2}$ and (e) is the scale production $P_{2,3}$. It is observed that $P_{1,2}$ and $P_{2,3}$ suppress most of the noise and well enhance the thin and wide vessels respectively. For a better visualization to show the effectiveness of scale production, we crop and zoom-in part of the images in FIG. 7, where (a) and (b) are cropped and enlarged from FIGS. 5 (a) and (b), and (c) is cropped and enlarged from FIG. (d). For the purpose of comparison, (d) in FIG. 7 shows the result by applying the max rule on the three response images. It is seen that scale production can better discriminate vessels from background noise while the max rule can introduce many false vessel pixels. FIG. 8 presents more examples to show the performance of scale production.

Thresholding

Three matched filters of variant scales are determined and then applied to the retinal image to obtain three responses. The responses are multiplied to obtain two scale production images, one in which the responses to vessel structures are enlarged in the other the responses to noise are weakened.

A simple single-thresholding or double-thresholding operation could effectively distinguish vessels from noise. Because double-thresholding can better suppress noise while preserving the connectivity of lines and edges, the present invention adopts double-thresholding and apply it to both $P_{1,2}$ and $P_{2,3}$. Take $P_{1,2}$ for example, with double-thresholding a low threshold $t_l$ and a high threshold $t_h = 2t_l$ are imposed on $P_{1,2}$ and then two vessels maps $V_l$ and $V_h$ are obtained. The final vessel map will be formed by selecting vessels in $V_l$ that link to the vessels in $V_h$. In the present invention, double-thresholding was implemented through morphological reconstruction.

Figure 9:
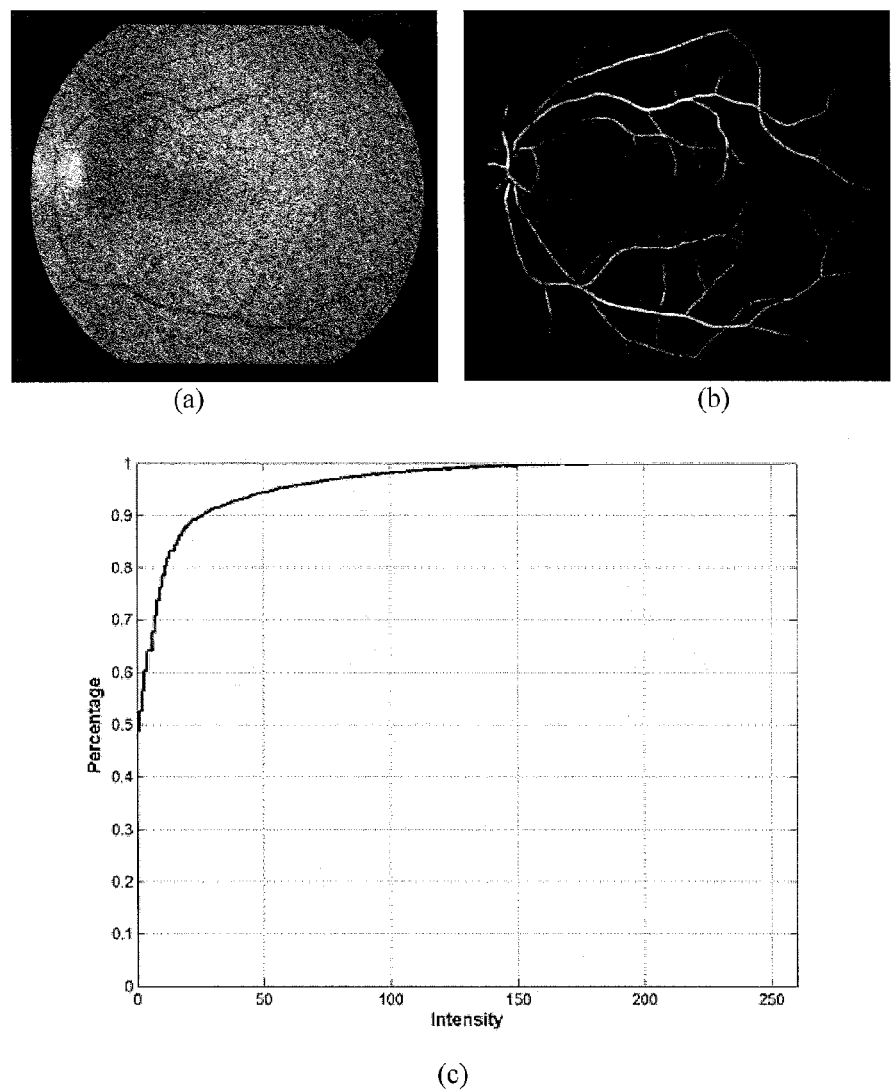
FIG. 9 shows amplitude distribution of the matched filters response of a retinal image.

A simple way to determine $t_l$ is to use the fact that the background area is normally the same for human beings. FIG. 9 presents an example of the amplitude distribution of the matched filter responses. In FIG. 9, (a) is an original image (f(x,y); (b) is its scale products of Gabor responses ($P^{s_j}(x,y)$); and (c) is the cumulative histogram of (b). By observing retinal images of large populations, the vessels occupy 10%~15% of a retina, which means the background is 85%~90%. Therefore we can set $t_l$ and $t_h$ based on the percentage of background area.

Another way is based on the fact that filter responses to noise and vessels should have different distributions. Suppose the background noise in retinal image f(x,y) is Gaussian white noise n(x,y) with zero mean and standard deviation $\upsilon$. The filters' responses to n(x,y) at two scales are $N_1(x,y)=g_1(x,y)*n(x,y)$ and $N_2(x,y)=g_2(x,y)*n(x,y)$. $N_1$ and $N_2$ are smoothed noise images and their standard deviations are respectively $\upsilon_1 = \|g_1\|\upsilon$ and $\upsilon_2 = \|g_2\|\upsilon$, where $\|g(x,y)\| = \sqrt{\iint g^2(x,y)dxdy}$ is the norm of the filter. $N_1$ and $N_2$ are jointly Gaussian distributed with correlation coefficient $$\rho_{1,2} = \frac{\iint g_1(x,y) \cdot g_2(x,y) dxdy}{\sqrt{\iint g_1^2(x,y) dxdy \cdot \iint g_2^2(x,y) dxdy}} \quad (3.6)$$

If the input image is pure noise n(x,y), the scale production will be $Z_{1,2}(x,y) = N_1(x,y) \cdot N_2(x,y)$. The probability density function (PDF) of $Z_{1,2}$ is $$Pr(z) = \frac{1}{\pi \Gamma(1/2) \sigma_1 \sigma_2 \sqrt{1-\rho^2}} \exp\left(\frac{\rho z}{(1-\rho^2)\sigma_1 \sigma_2}\right) K_0\left(\frac{|z|}{(1-\rho^2)\sigma_1 \sigma_2}\right) \quad (3.7)$$

where $\Gamma(t) = \int_0^\infty e^{-u} u^{t-1} du$ is the Gamma function and $K_0$ is the modified Bessel function of the second kind with order zero. The standard deviation of $Z_{1,2}$ is $$\kappa = \sqrt{E[z^2]} = \sqrt{1+2\rho_{1,2}^2} \cdot \upsilon_1 \upsilon_2 \quad (3.8)$$

We take $t_l = c\kappa$ as the low threshold to suppress $Z_{1,2}$ in $P_{1,2}$, where c is a constant. The values in $P_{1,2}$ below $t_l$ are removed as noise and the remaining values are extracted as vessel map $V_l \cdot t_h = 2c\kappa$ is then used to obtain another map $V_h$. Selecting the vessels in $V_l$ that link to the vessels in $V_h$ leads to the vessel map according to $P_{1,2}$. The same procedure goes to $P_{2,3}$ and the final vessel map is made by fusing the outputs of $P_{1,2}$ and $P_{2,3}$ with "OR" logic operation.

Post-Processing

Figure 10:
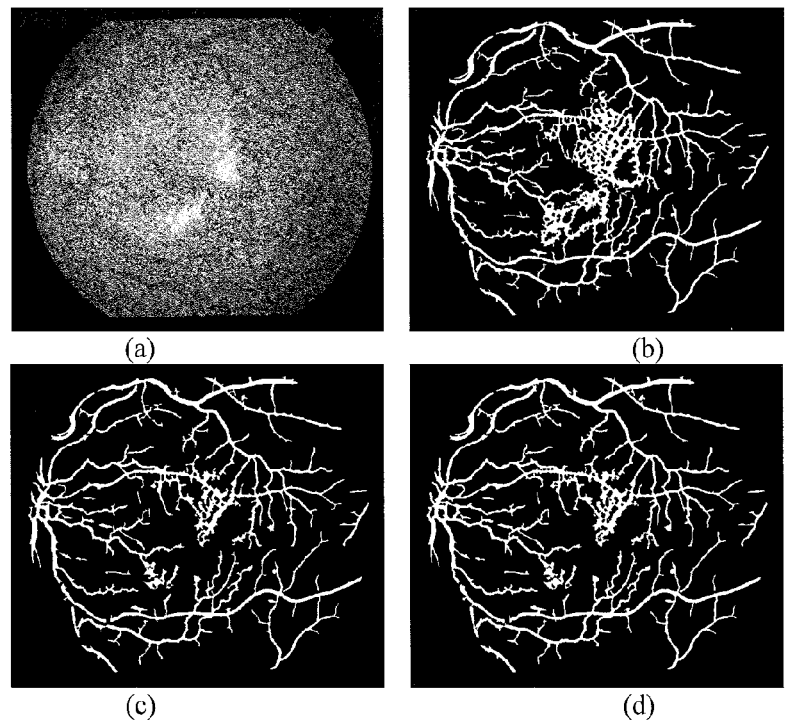
FIG. 10 shows vessel segmentation of a retinal image with bright lesions. (a) The original image with bright lesions in STARE database; (b) Vessel segmentation result by MPMF (Multiscale Production of the Matched Filter); (c) Suppress false positives caused by bright lesions; and (d) Link small broken vessels.

The MPMF works well for normal retinal images but not for abnormal (pathological) retinal images because retinal lesions may cause false positives. Therefore some post-processing operations are used to improve the segmentation accuracy. In FIGS. 10, (a) and (b) show an abnormal retinal image segmented by the proposed MPMF scheme. Two major problems are noted: (1) the false positives caused by bright lesions; and (2) some unlinked small vessels. To solve the two problems, simple post-processing procedures are implemented.

Eliminating the False Positives Caused by Bright Lesions

Because the matched filter responses not only to Gaussian-shaped lines but also to step edges, the bright lesions can cause false positives. As known in the art, the vessels were extracted by tracing parallel edges and each vessel pixel should have two edge pixels along the normal direction, and the gradient direction of each edge pixel should be the opposite of the other (both of them should normally point outward). This idea was adopted previously to suppress the matched filter response to bright lesions. In the present invention, this parallel-edge vessel model is adopted in the post-processing of the proposed MPMF scheme. For each vessel pixel classified by the MPMF, i.e. for each white pixel in FIG. 10 (b), we find the pair of boundary pixels along the normal direction of the vessel. The normal direction is defined as the direction with the maximum matched filter response. The boundary pixels are simply generated by subtracting FIG. 10 (b) from its dilated version. The gradient map is generated using a canny operator. If the gradient direction of both the two boundary pixels is pointing outward normal, the current vessel pixel is classified as a true positive. Otherwise it is a false positive. FIG. 10 (c) shows the false positive eliminating result of FIG. 10 (b).

Linking Broken Vessels

Figure 11:
FIG. 11 shows (a) and (c) as cropped and enlarged images from FIGS. 10 (a); (b) and (d) as cropped and enlarged images from FIG. 10 (d).

The broken vessels in FIG. (b) are caused by the vessels with discontinuous intensities, especially the small vessels whose intensities are very close to background. Even though the matched filter has already smoothed the intensity along the direction of the tangent of vessels, the matched filter responses of some pixels are still too weak to distinguish them from noise. Although the tacking based methods known in the art can somewhat improve the segmentation result, they are iterative and very time consuming. In the present invention, we use an anisotropic morphological operation to link the broken vessels segmented by MPMF. First, we segment the scale production using a very low threshold $t_{vl}=\alpha t_l$, where $\alpha$ is a constant (we set $\alpha=0.3$ in this paper). The pixels within interval $[t_{vl}, t_l]$ are defined as potential vessel pixels to be linked. At each potential vessel pixel, we apply morphological closing using a linear structure. The direction of the linear structure is perpendicular to the direction of the maximum matched filter response. In the experiments we set the length of the linear structure as 9 pixels. FIG. 10 (d) shows the vessel linking result of FIG. 10 (c). To show it more clearly, we have cropped and zoomed-in part of the images in FIG. 10 and show them in FIG. 11.

Experimental Results

Two sets of experiments are described in the following. In the first set, the scheme according to the present invention was applied to retinal images which were collected for diabetic retinopathy (DR) screening. In the second set, the scheme was applied to the STARE and DRIVE retinal image databases so as to make comparisons with other vessel extraction schemes.

Experiments on the Diabetic Retinal Images

The method of the present invention was applied to retinal images with DR to evaluate its performance in DR screening. These images were collected using a Kowa VK-3 fundus camera at 45° field of view (FOV) and stored in a 24-bit digital format. The spatial resolution of the images is 800×608 pixels. The appearance of Neovascularization (new vessels growth) stands for proliferative diabetic retinopathy, which is a very severe stage of DR. Neovasculars are small, thin vessels. If they can be automatically detected, it will be particularly helpful to the eye-care specialists in PDR diagnosis.

The MPMF scheme of the present invention was compared with three other state of the art schemes: the traditional matched filter developed by Chaudhuri et al; the scheme developed by Hoover et al; and a scheme that applies the max rule to the multiscale responses.

Figure 12:
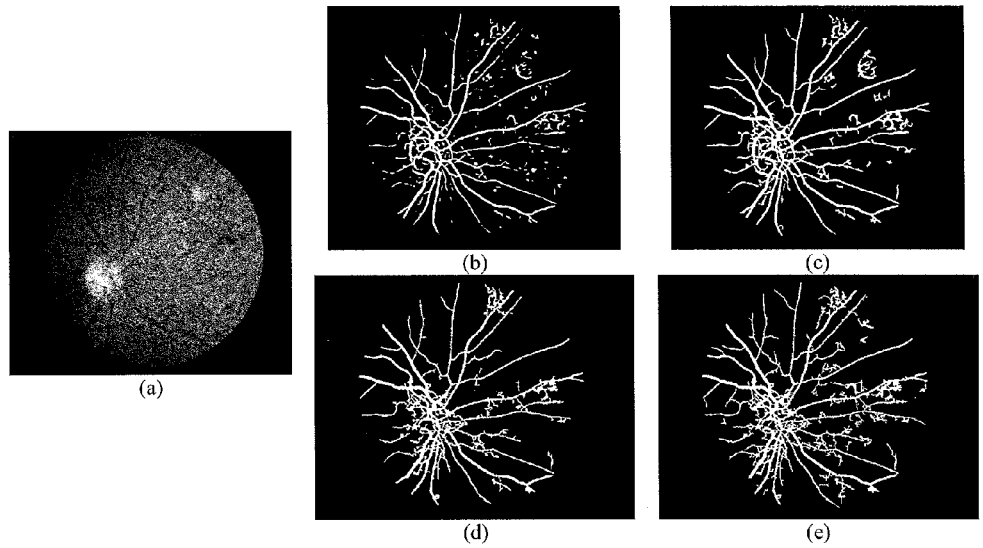
FIG. 12 shows the results obtained from different process methods: an original PDR image (a); the extracted vessel images using a prior art scheme by Chaudhuri (b); using another prior art scheme by Hoover (c); using the max rule with post-processing (d); and using MPMF with post-processing of the present invention (e).
Figure 13:
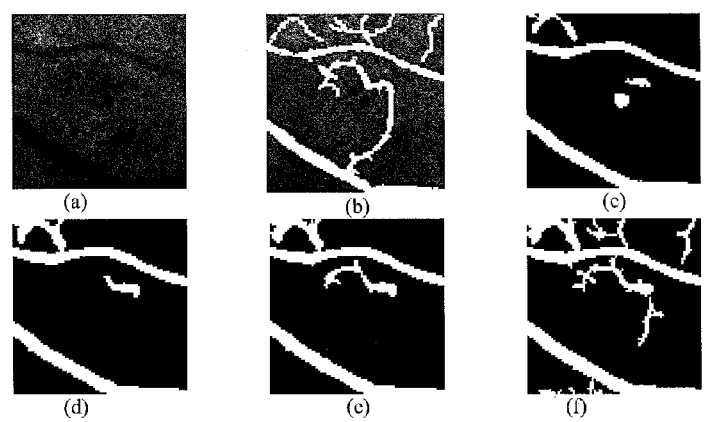
FIG. 13 is zoom-in images of FIG. 12. (a) Original image; (b) manually segmented image; (c)-(f) are corresponding to (b)-(e) of FIG. 12.
Figure 14:
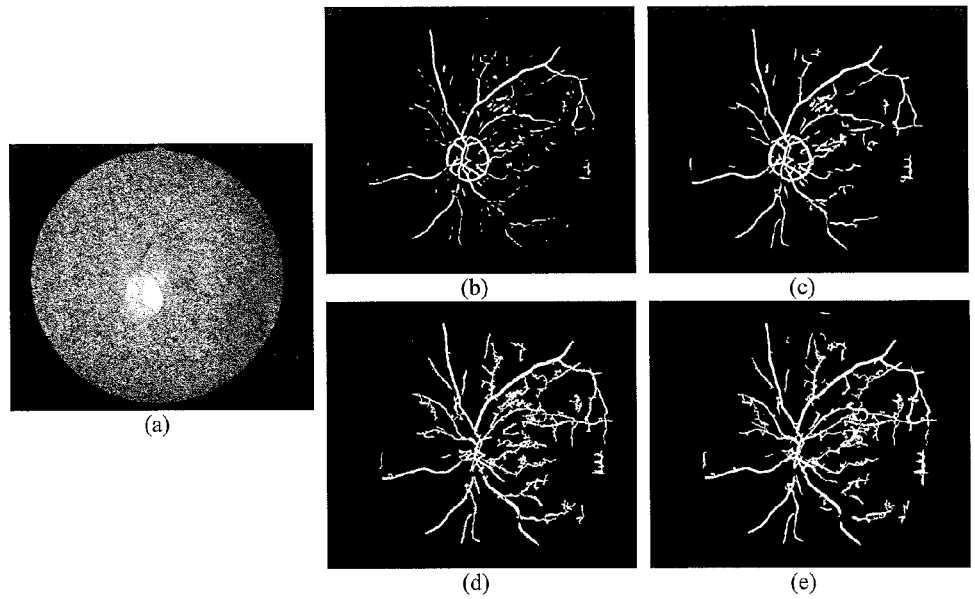
FIG. 14 shows a comparison among different possessing methods: an original PDR image (a); the extracted vessel images using schemes Chaudhuri (b); Hoover (c); the max rule with post-processing (d); and MPMF with post-processing of the present invention (e).
Figure 15:
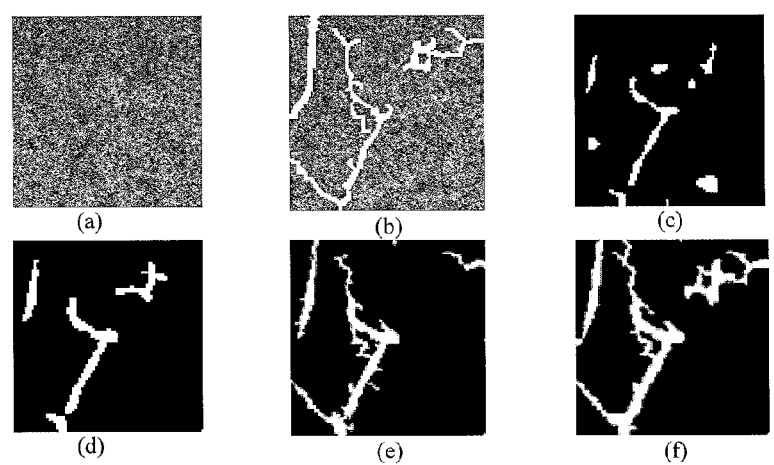
FIG. 15 shows zoom-in images of FIG. 14. (a) Original image; (b) manually segmented image; (c)-(f) corresponding to (b)-(e) in FIG. 14.

In FIG. 12, (a) shows a PDR retinal image; (b) shows the extracted vessel image using the matched filter; (c) is the output of method; (d) is the result obtained by using the max rule on three scales; and (d) is the vessel map obtained by using the MPMF method of the present invention. It can be seen that the MPMF extracted many weak, thin neovascular vessels, which cannot be detected by the other three schemes. To allow a better view, we cropped and zoomed-in part of the images, as in FIG. 13. It can be clearly seen that the abnormal fine neovascular structures could be effectively detected by using MPMF. FIG. 14 and FIG. 15 show another example of PDR.

Experiments on STARE and DRIVE Databases

In this section we test the proposed automated vessel segmentation method on the open STARE and DRIVE databases. The STARE database consists of retinal images captured with a TopCon TRV-50 fundus camera at 35° FOV, which were digitized at 24-bits and a spatial resolution of 700×605 pixels. We used a total of 20 images, ten from healthy ocular fundi and ten from unhealthy fundi. The database also provides hand-labeled images as the ground truth for vessel segmentation so that the algorithms can be evaluated for comparison. The DRIVE databases consists of 40 images captured with a Canon CR5 camera at 45° FOV, which were digitized at 24-bits with a spatial resolution of 565×584 pixels. Seven of the images are pathological. Hand-labeled images are also available in this database.

It is not possible to make a valid comparison of the four methods in question here by simply directly matching the segmented vessel map with the ground-truth. This is because large vessels are both easier to detect and make up most of the white pixels in the ground truth and some methods may be better at the task of identifying large vessels but not small vessels. So, in order to create a task in which the methods must be able to detect both large and small vessels, we carried out the matching only after thinning the segmented and ground truth images. We then calculated the sensitivity against predictive value, which is defined as following.

Because the same vessel may not be matched in the precision of one pixel after thinning, we dilate the thinned images for matching, which means that the true positives (TP), vessel pixels correctly classified, are defined as $$TP = \#[S(\delta^B(v_m) \wedge v_c)] \quad (3.9)$$

where # means "the number of", S(f) is the support of f, $\delta^B(f)$ means dilating f using structure element B, $\wedge$ is the logical "and" operation, $v_m$ is the manually segmented vessel, and $v_c$ is the automated segmentation result. Here we set B as a disc with 1 pixel radius. The false positives (FP), background pixels classified as vessel pixels, and false negatives (FN), vessel pixels classified as background pixels, are defined as $$FP = \#[S(v_c) \backslash S(\delta^B(v_m) \wedge v_c)] \quad (3.10)$$

$$FN = \#[S(v_m) \backslash S(v_m \wedge \delta^B(v_c))] \quad (3.11)$$

where \ is the set difference. Because in the thinned images, the FP will be always very small, we plot sensitivity against predictive value to evaluate the performance. The sensitivity and predictive value are defined as $$\text{sensitivity} = \frac{TP}{TP + FN} \quad (3.12)$$

$$\text{predictive value} = \frac{TP}{TP + FP} \quad (3.13)$$

The sensitivity is the rate of correctly classified vessel pixels. The predictive value is the probability that a pixel that has been classified as a vessel really is a vessel. We compare MPMF with single scale matched filter and multiscale matched filters fusing by maximum rule. All of these three kinds of filter responses are thresholded by double-thresholding without any postprocessing so that we can clearly see the improvements to be had from different fusion strategies.

Figure 16:
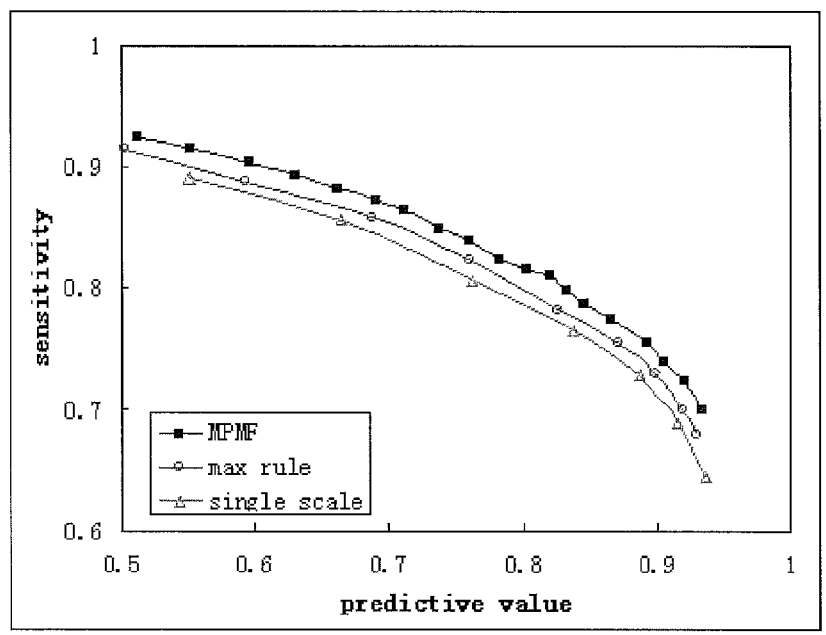
FIG. 16 shows sensitivity vs. predictive value. (a) STARE database; (b) DRIVE database.
Figure 16:
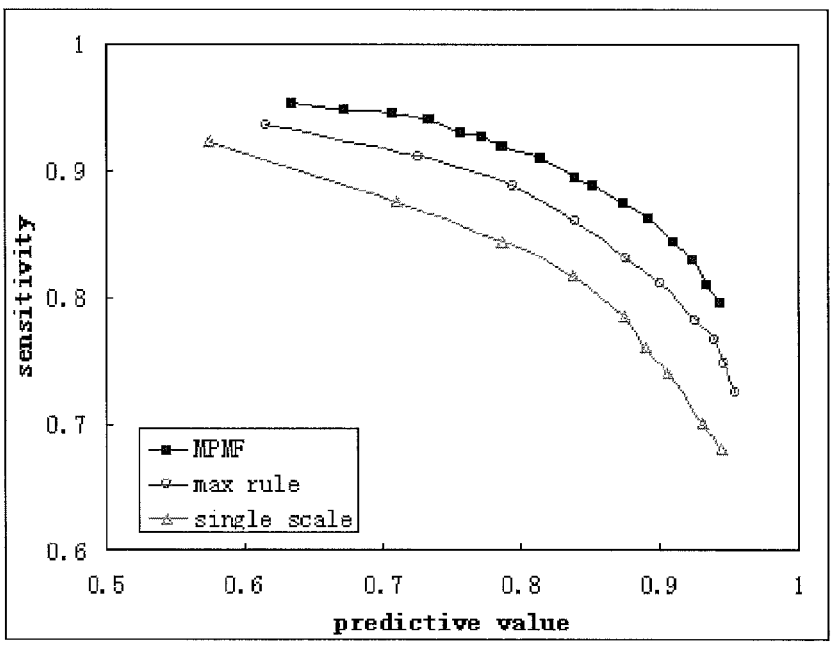

The 10 normal images in STARE database and the ground truth generated by the second human expert (labels-vk) are used to plot the sensitivity against predictive value shown in FIG. 16 (a). The 16 normal images in DRIVE database and the ground truth generated by the second human expert (2nd_manual) are used to plot the sensitivity against predictive value shown in FIG. 16 (b). The different values of sensitivity and predictive values are generated by varying the value of. (Scale production is a strategy to improve signal-to-noise ratio but the matched filter produce high responses to lesions. Therefore we only use normal images in this experiment to demonstrate the efficiency of scale production.)

Tables 3.1-3.3 compare our method (MPMF plus postprocessing) with the state-of-the-art schemes by using three performance measures (1) detection accuracy, and the corresponding (2) true positive rate (TPR) and (3) false positive rate (FPR) at that accuracy. The detection accuracy is defined as the ratio of the total number of correctly classified pixels (the vessel pixels classified as vessel pixels and the non-vessel pixels classified as non-vessel pixels) to the number of pixels inside FOV. The TPR is defined as the ratio of the number of correctly classified vessel pixels to the number of total vessel pixels in the ground truth. The FPR is defined as the ratio of the number of non-vessel pixels inside FOV but classified as vessel pixels to the number of non-vessel pixels inside FOV in the ground truth.

Table 3.1 presents the performance of our method on the STARE database. The performance measures of Staal, Mendonca, and Martinez-Perez were obtained from their papers. The performance measures of Soares and Hoover were calculated using the segmented images obtained from their websites. The FOV used for STARE database is generated using the code provided by Soares. All 20 images are used for the experiment. The images hand-labeled by the first human expert (labels-ah) are used as ground truth.

Table 3.2 presents the performance of our method for DRIVE database. The performance measures of Staal and Soares were calculated using the segmented images obtained from their websites. The performance measures of Mendonca and Martinez-Pérez were obtained from their papers. The DRIVE database provides FOV. All 20 images in the test set are used for the experiment. The images hand-labeled by the first human expert (2nd_manual) are used as ground truth.

Table 3.3 presents the different performances of our method for normal and abnormal images in STARE database. The performance measures of Soares and Hoover were calculated using the segmented images obtained from their websites. The performance measure of Mendonça was obtained from that paper.

From Tables 3.1-3.3, we can see that the proposed MPMF method is competitive with those state-of-the-art methods. It achieves very high TPR, especially for the normal retinal images. It should be noted that the proposed MPMF method is much easier to implement and has much lower complexity than the snake and tracking based classification methods and the supervised methods. This makes the building of a real-time system possible. The execution time for processing one retinal image is around 20 seconds (Matlab programming environment without optimization, Pentium III 1.0 GHz CPU, and 512 MB memory).

TABLE 3.1

Extraction Results for 20 Images in STARE Database

| Method | Accuracy | TPR | FPR |
| --- | --- | --- | --- |
| $2^{nd}$ Human observer | 0.9354 | 0.8949 | 0.0610 |
| Hoover | 0.9267 | 0.6751 | 0.0433 |
| Staal | 0.9516 | 0.6970 | 0.0190 |
| Soares | 0.9485 | 0.7211 | 0.0235 |
| Mendonça | 0.9479 | 0.7123 | 0.0242 |
| Martinez-Pérez | 0.9410 | 0.7506 | 0.0431 |
| MPMF | 0.9436 | 0.7390 | 0.0289 |

TABLE 3.2

Extraction Results for 20 Images (Test Set) in DRIVE Database

| Method | Accuracy | TPR | FPR |
| --- | --- | --- | --- |
| $2^{nd}$ Human observer | 0.9473 | 0.7761 | 0.0275 |
| Staal | 0.9442 | 0.7194 | 0.0227 |
| Soares | 0.9466 | 0.7283 | 0.0212 |
| Mendonça | 0.9463 | 0.7315 | 0.0219 |
| Martinez-Pérez | 0.9344 | 0.7246 | 0.0345 |
| MPMF | 0.9396 | 0.7368 | 0.0262 |

TABLE 3.3

Extraction Results for 20 Images in STARE Database (Normal versus Abnormal Cases)

| Method | Accuracy | TPR | FPR |
| --- | --- | --- | --- |
| Normal cases | | | |
| $2^{nd}$ Human observer | 0.9283 | 0.9646 | 0.0764 |
| Hoover | 0.9324 | 0.6766 | 0.0338 |
| Soares | 0.9467 | 0.7325 | 0.0261 |
| Mendonça | 0.9531 | 0.7366 | 0.0178 |
| MPMF | 0.9546 | 0.8130 | 0.0263 |
| Abnormal cases | | | |
| $2^{nd}$ Human observer | 0.9425 | 0.8252 | 0.0456 |
| Hoover | 0.9211 | 0.6736 | 0.0528 |
| Soares | 0.9504 | 0.7096 | 0.0206 |
| Mendonça | 0.9426 | 0.6801 | 0.0306 |
| MPMF | 0.9327 | 0.6650 | 0.0314 |

Figure 17:
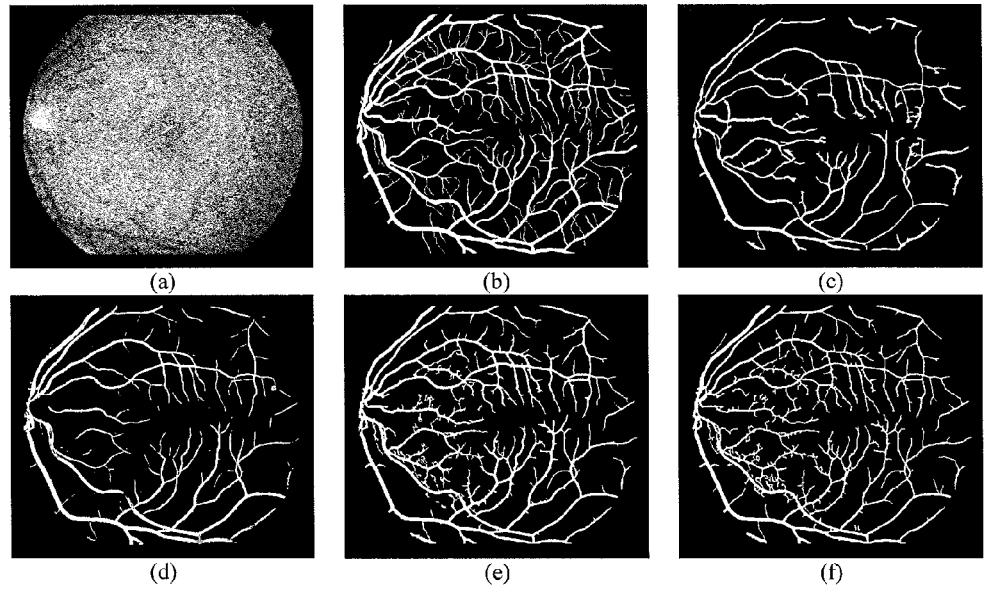
FIG. 17 shows the original image im0077 in the STARE database (a); the ground truth vessel map (b); the extraction results by Hoover (c) [Accuracy=0.8984, Sensitivity=0.5652, Predictive=0.9399]; by Sores (d) [Accuracy=0.9282, Sensitivity=0.5917, Predictive=0.9410]; by the max rule (e) [Accuracy=0.9272, Sensitivity=0.7259, Predictive=0.8972]; and by MPMF of the present invention (f) [Accuracy=0.9229, Sensitivity=0.7482, Predictive=0.9069].
Figure 18:
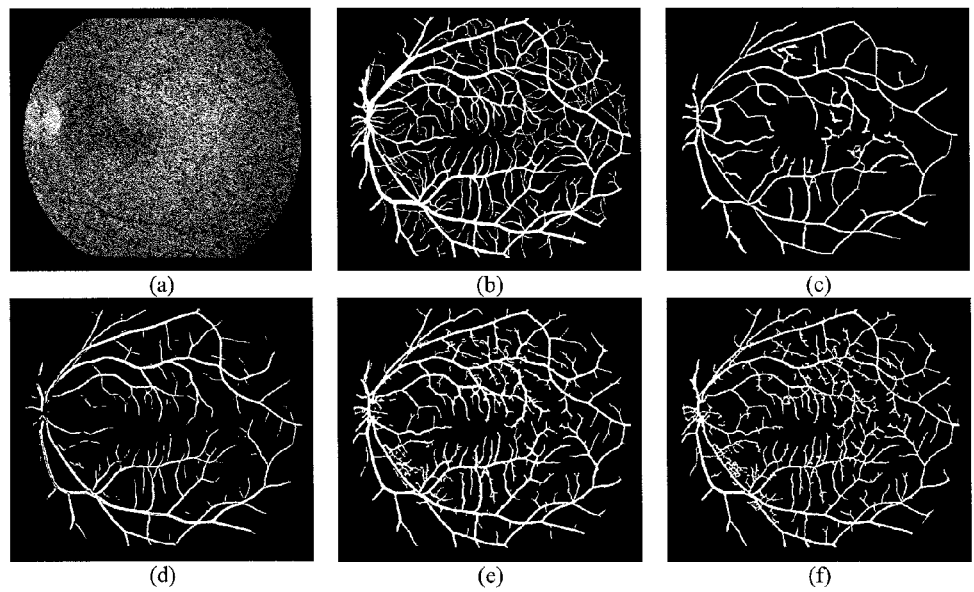
FIG. 18 shows the original image im0255 in the STARE database (a); the ground truth vessel map (b); the extraction results by Hoover (c) [Accuracy=0.8932, Sensitivity=0.4664, Predictive=0.9322]; by Sores (d) [Accuracy=0.9117, Sensitivity 0.5144, Predictive=0.9461]; by the max rule (e) [Accuracy=0.9218, Sensitivity=0.6957, Predictive=0.8991]; and by MPMF of present invention [Accuracy=0.9204, Sensitivity=0.7169, Predictive=0.9060].

FIGS. 17-18 show the vessel segmentation results on two retinal images (im0077, and im0255) in the STARE database using the four schemes: the Staa and Soares schemes, max rule and the MPMF of the present invention. The segmented results of Hoover and Soares were obtained from their websites. We varied the threshold to achieve the greatest sensitivity at the smallest cost of accuracy. The MPMF method achieves the highest sensitivity at an accuracy similar to other schemes. It can be seen that the matched filter scheme in Hoover misses many thin vessels; the multiscale scheme with the max rule extracts some thin vessels but also introduces some false vessels due to noise; the MPMF scheme can find many weak and thin vessels which cannot be found by the other three schemes. It also does a good job of suppressing false vessels caused by background noise.

Figure 19:
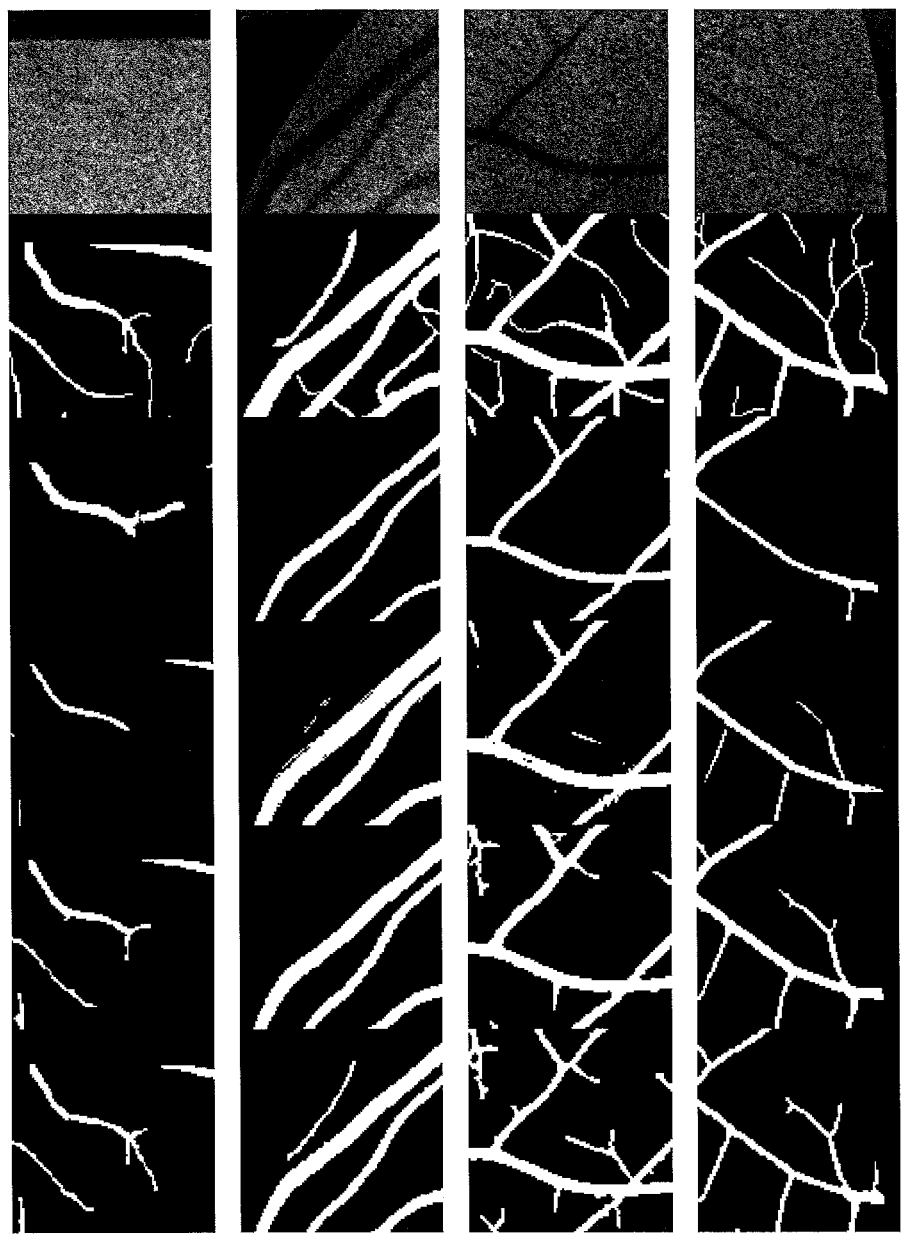
FIG. 19 is zoom-in subimages from in FIG. 18. The first row shows some cropped blocks from the original images; the second row shows their corresponding ground truth vessel maps; the third row shows the vessel extraction results using method by Hoover; the fourth row shows the results using method by Soares; the fifth row shows the results using the multiscale max rule; and the sixth row shows the results using the MPMF method of the present invention.

To show the result more clearly, we cropped several parts of the images in FIGS. 17-18 and zoomed-in in FIG. 19. The first row shows the original cropped images; the second row shows their corresponding ground truth vessel maps; the third row shows the vessel extraction results when using the matched filter scheme by Hoover; the fourth row shows the results using Soares' supervised method; the fifth row shows the results by using the Max rule over three scales; the bottom row shows the results of MPMF. We see that MPMF scheme can extract both thin and wide vessels simultaneously. The low contrast weak vessel can also be extracted from the noisy background using MPMF. In addition, MPMF can also preserve better vessel width information.

Figure 20:
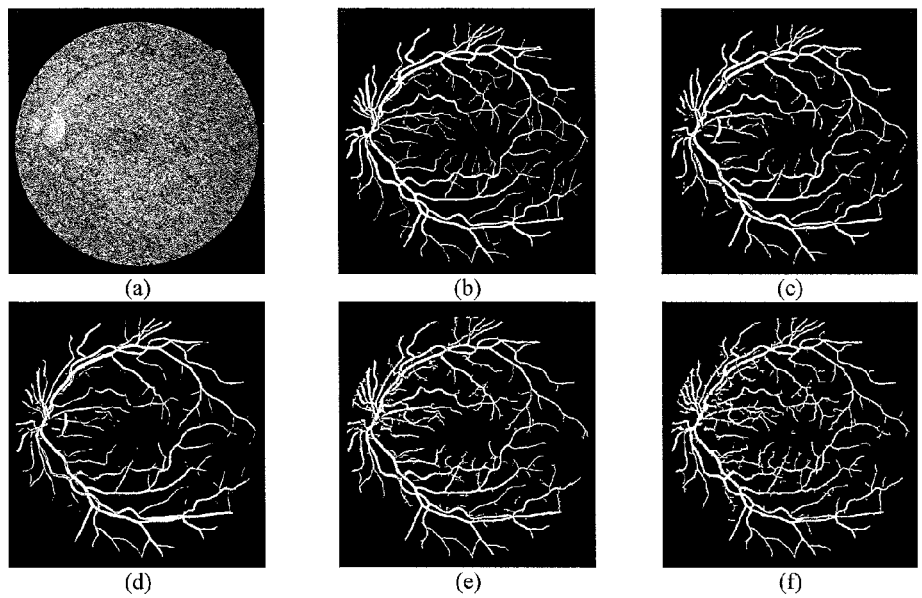
FIG. 20 shows the original image 01_test in the DRIVE database (a); the ground truth vessel map (b); the extraction results by Staal (c) [Accuracy=0.9495, Sensitivity=0.8143, Predictive=0.9696]; by Sores (d) [Accuracy=0.9495, Sensitivity=0.7939, Predictive=0.9542]; by the max rule (e) [Accuracy=0.9441, Sensitivity=0.8601, Predictive=0.8681]; and by the MPMF method of the present invention [Accuracy=0.9406, Sensitivity=0.8806, Predictive=0.8649].
Figure 21:
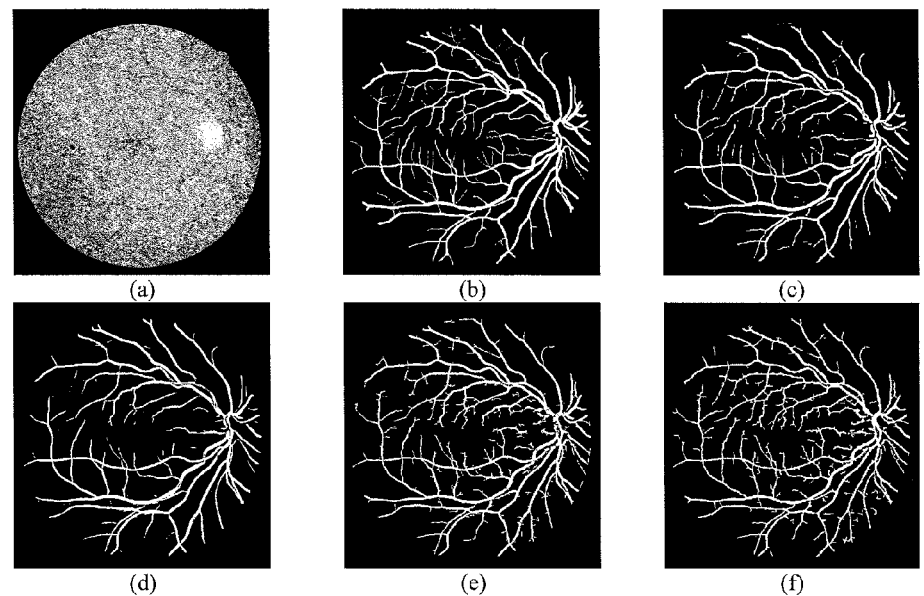
FIG. 21 shows the original image 02_test in DRIVE database (a); the ground truth vessel map (b); the extraction results by Staal (c) [Accuracy=0.9564, Sensitivity=0.8273, Predictive=0.9678]; by Soares (d) [Accuracy=0.9529, Sensitivity=0.7777, Predictive=0.9582]; by the max rule (e) [Accuracy=0.9467, Sensitivity=0.8618, Predictive=0.8450]; and by the MPMF method of the present invention [Accuracy=0.9426, Sensitivity=0.9025, Predictive=0.8622].
Figure 22:
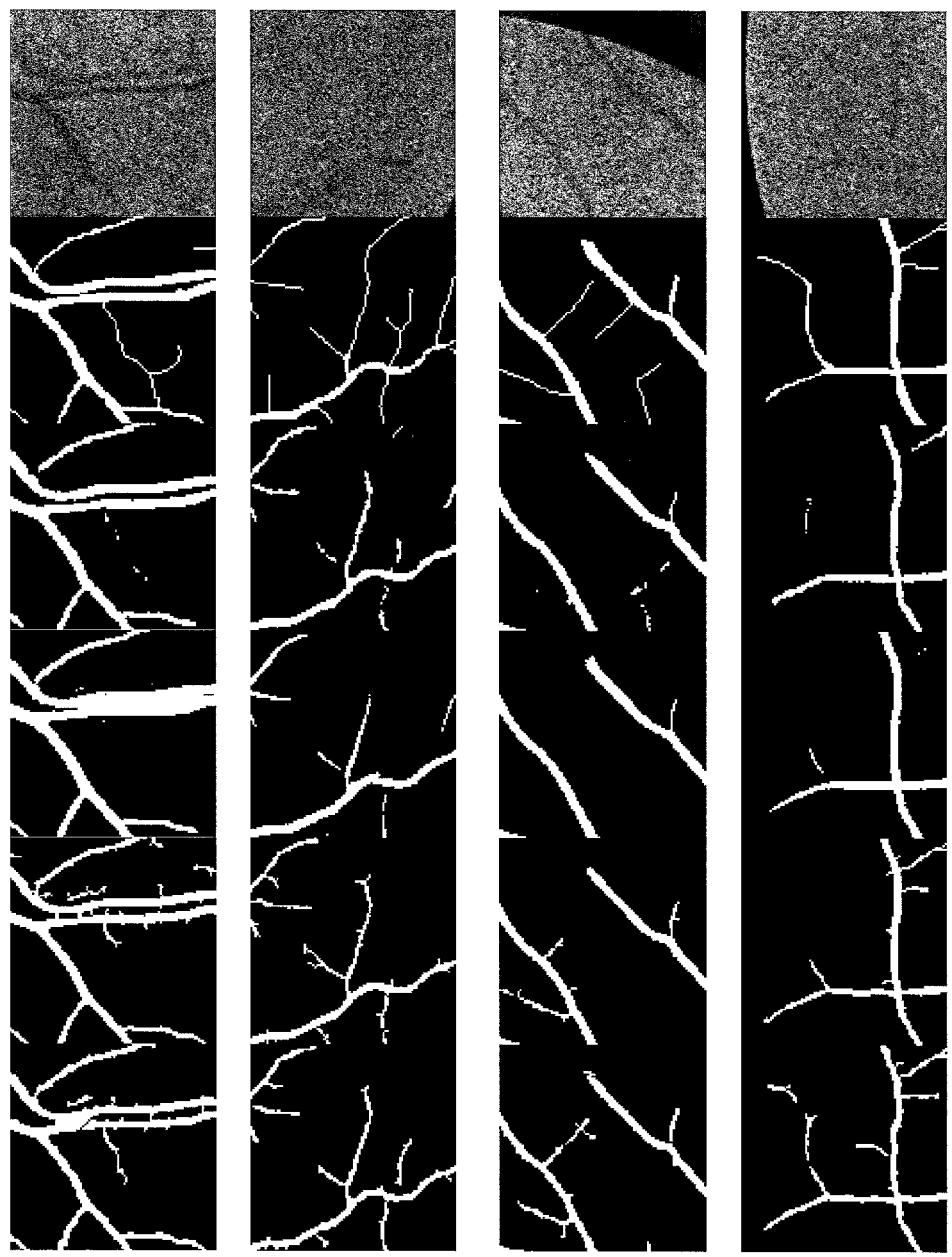
FIG. 22 shows zoom-in subimages from FIG. 21. The first row shows some cropped blocks from the original images; the second row shows their corresponding ground truth vessel maps; the third row shows the vessel extraction results using the method of Staal; the fourth row shows the results using the method of Soares; the fifth row shows the results using the multiscale max rule; and the sixth row shows the results using the MPMF method.

FIGS. 20 and 21 show the vessel segmentation results on two retinal images (01_test, and 02_test) in the DRIVE database using four schemes: the Staa and Soares schemes, max rule and the MPMF of the present invention. The segmented results of Staal and Sores were obtained from their websites. The cropped and zoomed-in images are shown in FIG. 21.

Segmentation of Retinal Vessels Using MMFDST

The importance and effectiveness of using retinal vessels in screening Diabetic Retinopathy (DR) are known in the art. As a serious stage of DR, Proliferative Diabetic Retinopathy (PDR) is a common complication of diabetes that damages the eye's retina and an early diagnosis of PDR is critical to protecting patients' vision. Because the appearance of neovascular (new vessel growth) stands for PDR, the false positives of vessels will distort the diagnosis a lot. Here, we will describe a retinal vessel segmentation scheme using Modified Matched Filter and Double Site Thresholding (MMFDST), which can suppress the false positives efficiently.

Many retinal vessel extraction methods have been proposed in the art yet neovascular extraction is still a difficult problem in terms of accuracy. In the present invention we propose a modified matched filter that suppresses the false detections caused by bright blobs. Instead of subtracting the local mean from the response for removing background and then thresholding to detect vessels as in the traditional matched filter, we first enhance the retinal image by using Gaussian filters and then analyze the local structures of filtering outputs by a double-side thresholding operation. This modified matched filter could avoid responding to non-line edges, which would significantly reduce the false detection of vessels.

Figure 23:
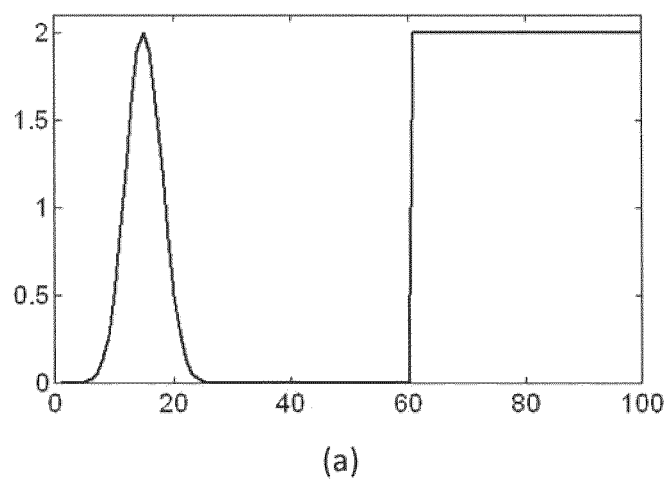
FIG. 23 shows responses of different line detectors to a Gaussian line cross-section and an ideal step edge. (a) a Gaussian line cross-section and an ideal step edge; (b-1) the second order derivative of Gaussian and (b-2) its filter response; (c-1) Gabor filter and (c-2) its filter response; (d-1) matched filter and (d-2) its filter response.
Figure 23:
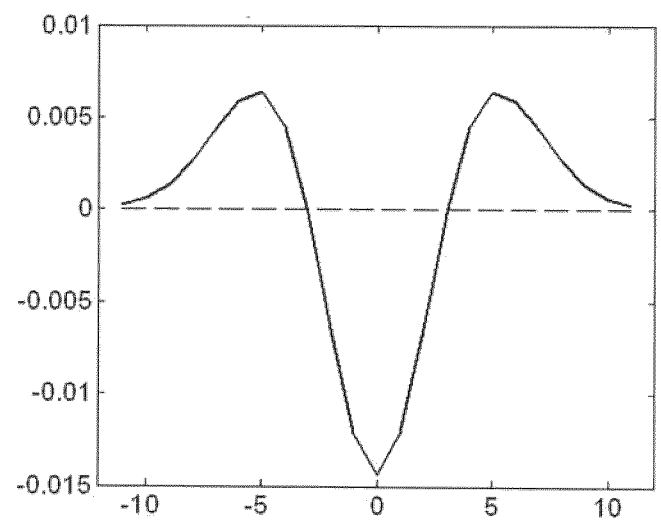
Figure 23:
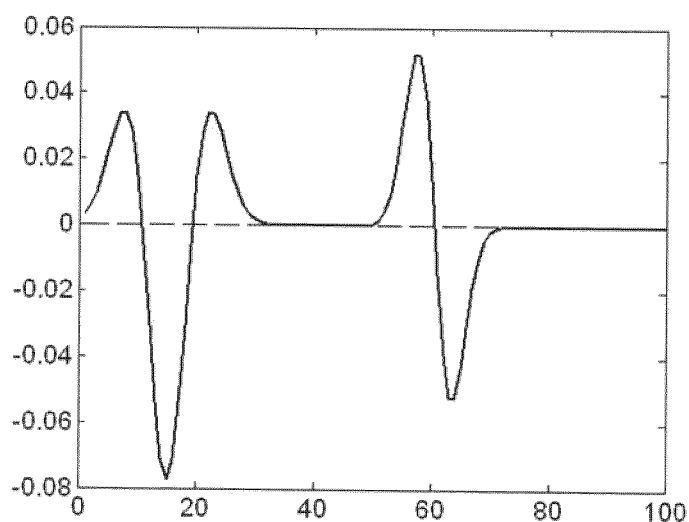
Figure 23:
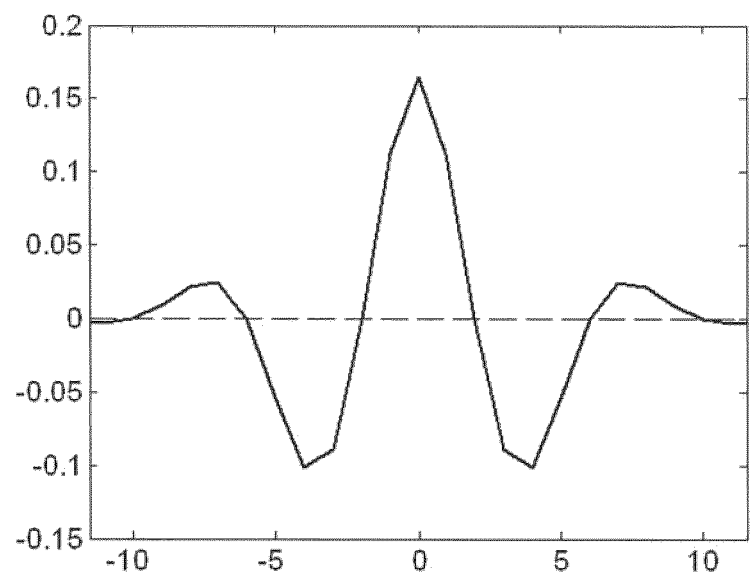
Figure 23:
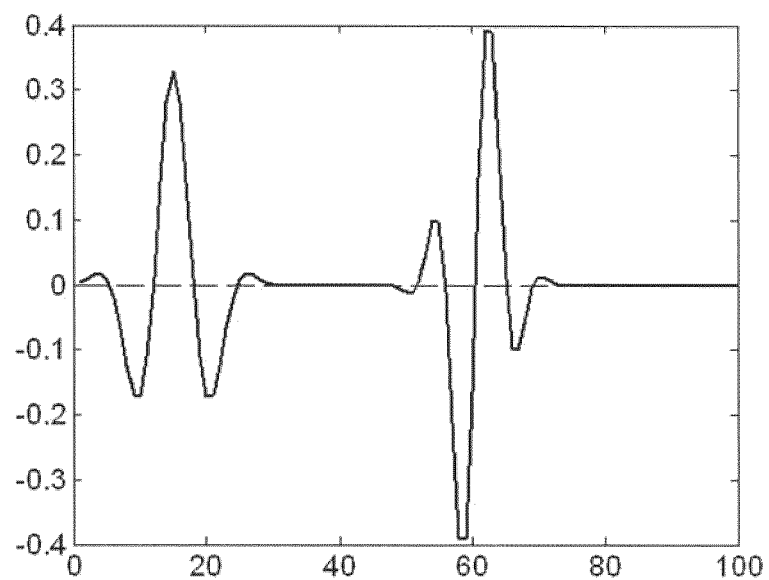
Figure 23:
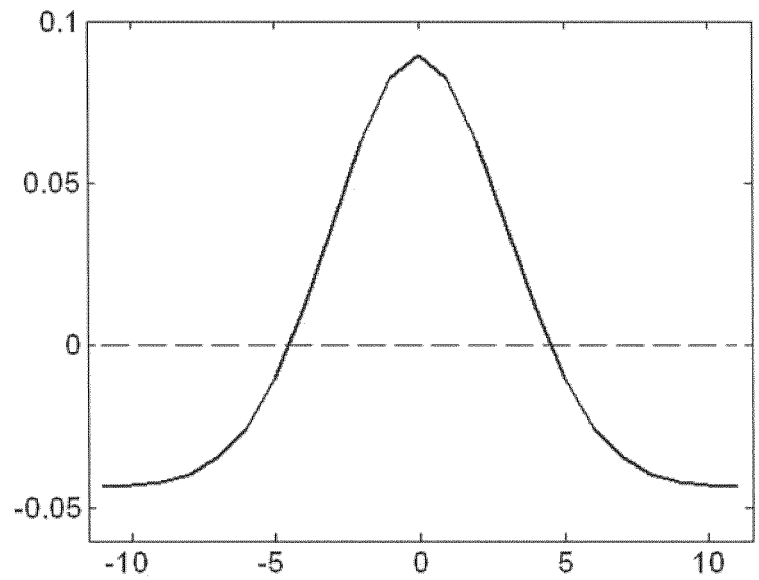
Figure 23:
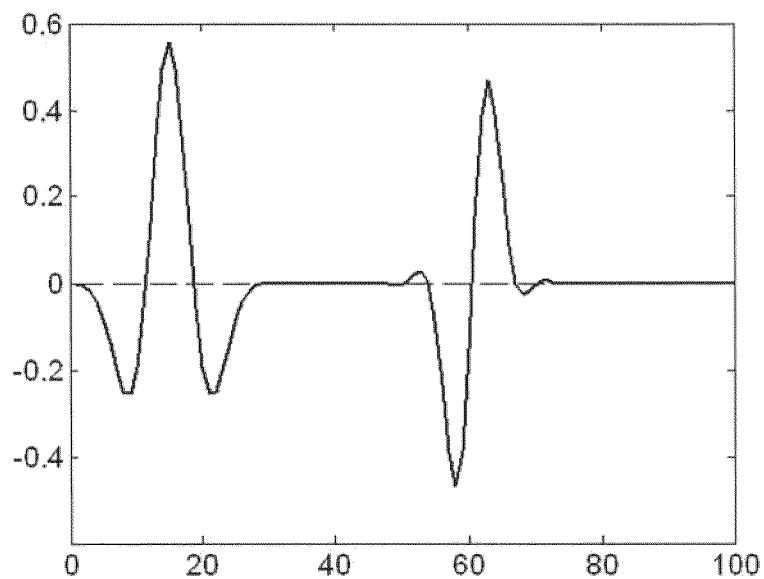
Figure 24:
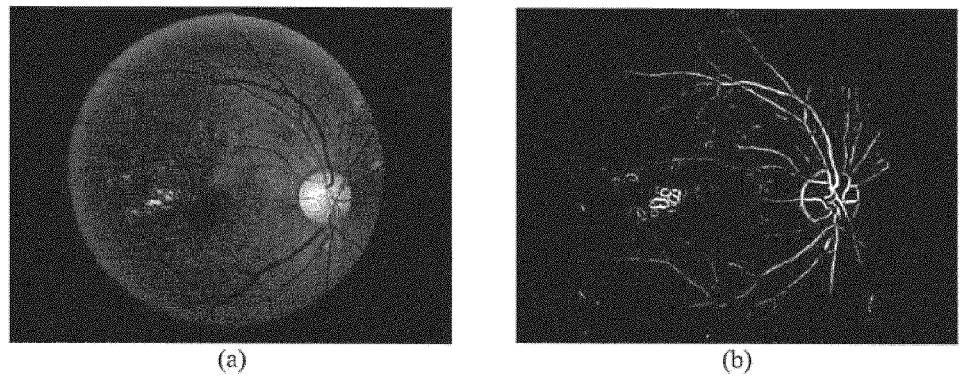
FIG. 24 shows a retinal image with NPDR (Non-Proliferative Diabetic Retinopathy) (a); its matched filter response (b).

One major problem of the matched filter is that it responds not only to lines but also non-line edges. This problem also exists in other line detectors such as the Gabor filter and the second order derivative of a Gaussian function. FIG. 23 illustrates this by showing the responses of different filters to a Gaussian function (i.e. the cross-section of a vessel) and an ideal step edge. It can be seen that all three filters have strong responses to both the line cross-section and the non-line ideal step edge. FIG. 24 shows the response image of the matched filter to a retinal image. Therefore, in pathological images, the strong responses to the vessels are clear, as well as the edges of the bright lesions. After thresholding, both the vessels and the edges of lesions will be detected.

Modified Matched Filter with Double-Side Thresholding

In the definition of matched filter in Equation (3.1), the mean value m is subtracted from the Gaussian function to remove the smooth background in the filtering output. Then a thresholding operation can be used to detect the vessel pixels. However, as shown in FIG. 24, the matched filter will also give strong response to non-vessel edge structures (bright lesions, dark lesions) and the thresholding cannot distinguish them well from the vessel structures. Here, we present a new scheme to solve this problem. We don't subtract the mean from the Gaussian filter and modify the matched filter in (3.1) as $$g(x,y) = \exp(-x^2/\sigma^2), \text{ for } |x| \leq 3\sigma, |y| \leq L/2 \quad (3.14)$$

Figure 25:
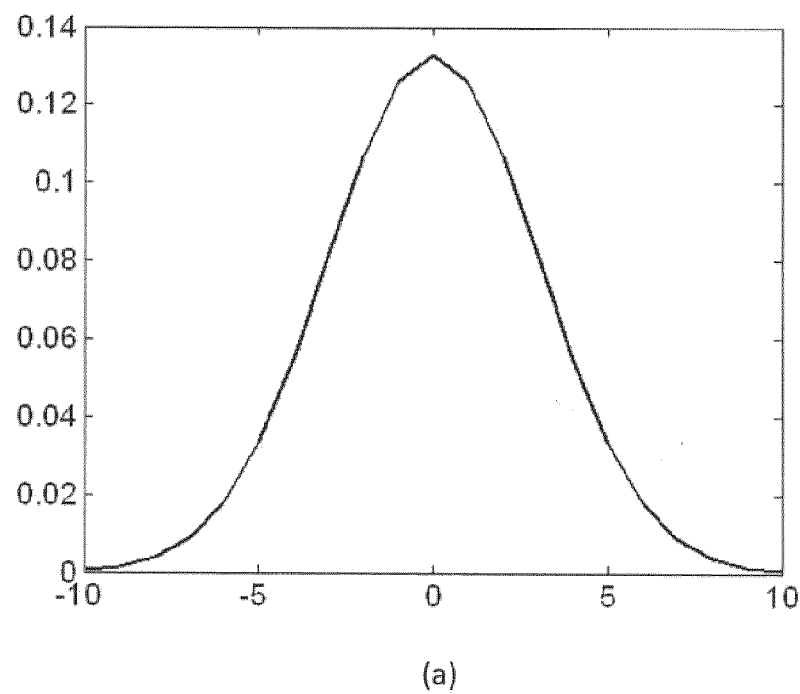
FIG. 25 shows the results with the modified matched filter in 1D (a) and 2D (b); (c) a Gaussian function and a step edge with noise; (d) the modified matched filter's response to the signal in (c).

This 2D modified matched filter in (3.14) is a truncated Gaussian function in x direction and the Gaussian function repeats in y direction. FIGS. 25 (a) and (b) show the 1D cross-section of the filter and the 2D filter along 4 different directions. FIGS. 25 (c) and (d) show a 1D noisy signal, which contains a Gaussian function and a step edge, and its filtering response.

For the convenience of analysis, the modified matched filter will be applied to the complement of the original retinal image, in which the vessels are brighter than the background. The image will be filtered by g(x,y) along 8 directions. Each of the 8 filtering responses will be thresholded to generate a vessel map. Finally the 8 vessels maps are fused through a logical 'OR' operation. Next we introduce the proposed thresholding strategy.

Double-Site Thresholding

After image enhancement by using the modified matched filters, the pixels must be classified as either vessel or non-vessel pixels. To classify pixels with suppressing the false positives of vessels, we propose here a local double-side thresholding scheme to segment the retinal image. To simplify the analysis of filter responses for thresholding, we consider the 1D case, i.e. a 1D signal f(x) is convolved with the 1D matched filter g(x): r(x)=f(x)*g(x). Referring to FIG. 25 (d), we can see that if r(x) is the peak point of a Gaussian shaped cross-section of a vessel, it should be greater than both its left and right neighboring points. If r(x) is from the non-vessel edges, it will not be much greater than its neighbors in both sides. Based on this observation, the vessels and non-vessel edges can be distinguished.

Taking this into account, we define that a point r(x) is a vessel point if it is greater than its neighbors r(x−d) and r(x+d) with a threshold T. Mathematically, there is:

$$\begin{cases} r(x) - r(x-d) > T \\ r(x) - r(x+d) > T \end{cases} \quad (3.15)$$

where d is a parameter concerning the width of the vessel to be detected and T is a threshold to evaluate the vessel points.

Obviously, one key issue in (3.15) is the determination of parameters d and T. These two parameters are not independent. We use a matched filter g(x) with standard deviation (std) σ to detect the vessels whose Gaussian-shaped cross-sections have std around σ. Thus we can set $$d = c_d \cdot \sigma \quad (3.16)$$

where $c_d$ is a constant. In this example, we set it about 2.

Suppose the std of the Gaussian-shaped vessel cross-section f(x) to be detected by g(x) is also σ, the filtering output r(x) will still be a Gaussian function, and its std will be $\sigma_r = \sqrt{\sigma^2 + \sigma^2} = \sqrt{2}\sigma$. Denote $x_0$ the peak point of r(x). It can be easily calculated that $$r(x_0) - r(x_0 - d) = r(x_0) - r(x_0 + d) \quad (3.17)$$
$$= \frac{1}{\sqrt{2\pi}\,\sigma_r}\left(1 - \exp\left(-\frac{d^2}{2\sigma_r^2}\right)\right)$$
$$= \frac{1}{2\sqrt{\pi}\,\sigma}\left(1 - \exp\left(-\frac{d^2}{4\sigma^2}\right)\right)$$

Denoting $$\Gamma = \frac{1}{2\sqrt{\pi}\,\sigma}\left(1 - \exp\left(-\frac{d^2}{4\sigma^2}\right)\right),$$

for a point $x_1$ in the neighborhood of $x_0$, we can see that $r(x_1) - r(x_1 - d) < \Gamma$ and $r(x_1) - r(x_1 + d) < \Gamma$. Thus to detect point $x_0$ and its neighbors, which are considered as vessel points, we set the threshold T in (3.15) as $$T = c_T \cdot \Gamma \quad (3.18)$$

where $c_T$ is a constant and $c_T<1$. In this work, we choose $0.5<c_T<0.8$.

One way of producing better segmentation results is to adopt the double-thresholding strategy. A low threshold $T_l=c_T \cdot F$ and a high threshold $T_h=2T_l$ are set and then two vessels maps $V_l$ and $V_h$ are obtained. The final vessel map will be formed by selecting vessels in $V_l$ that link to the vessels in $V_h$. Another way is to use multiple filters g(x,y) at multiple scales to detect vessels of different widths. For example, we can use two filters, $g_1$ with std $\sigma_1$ and $g_2$ with std $\sigma_2$, to implement the vessel detection procedure described above. This gives us two vessel maps, denoted by $V_1$ and $V_2$, which we can fuse using the "OR" logic operation to produce a more robust vessel map.

Experimental Results

This section presents the experimental results of our method. Two databases, ZUEYE and STARE, are used for our experiments. The indices that used to quantitatively measure the performance of different algorithms include: (1) detection accuracy (ACC); (2) the corresponding true positive rate (TPR) and (3) the false positive rate (FPR) at that accuracy. The ACC is defined as the ratio of the total number of correctly classified pixels (the vessel pixels classified as vessel pixels and the non-vessel pixels classified as non-vessel pixels) to the number of pixels inside FOV; the TPR is defined as the ratio of the number of correctly classified vessel pixels to the number of total vessel pixels in the ground truth; the FPR is defined as the ratio of the number of non-vessel pixels inside field of view (FOV) but classified as vessel pixels to the number of non-vessel pixels inside FOV in the ground truth.

Evaluation on the ZUEYE Database

Figure 26:
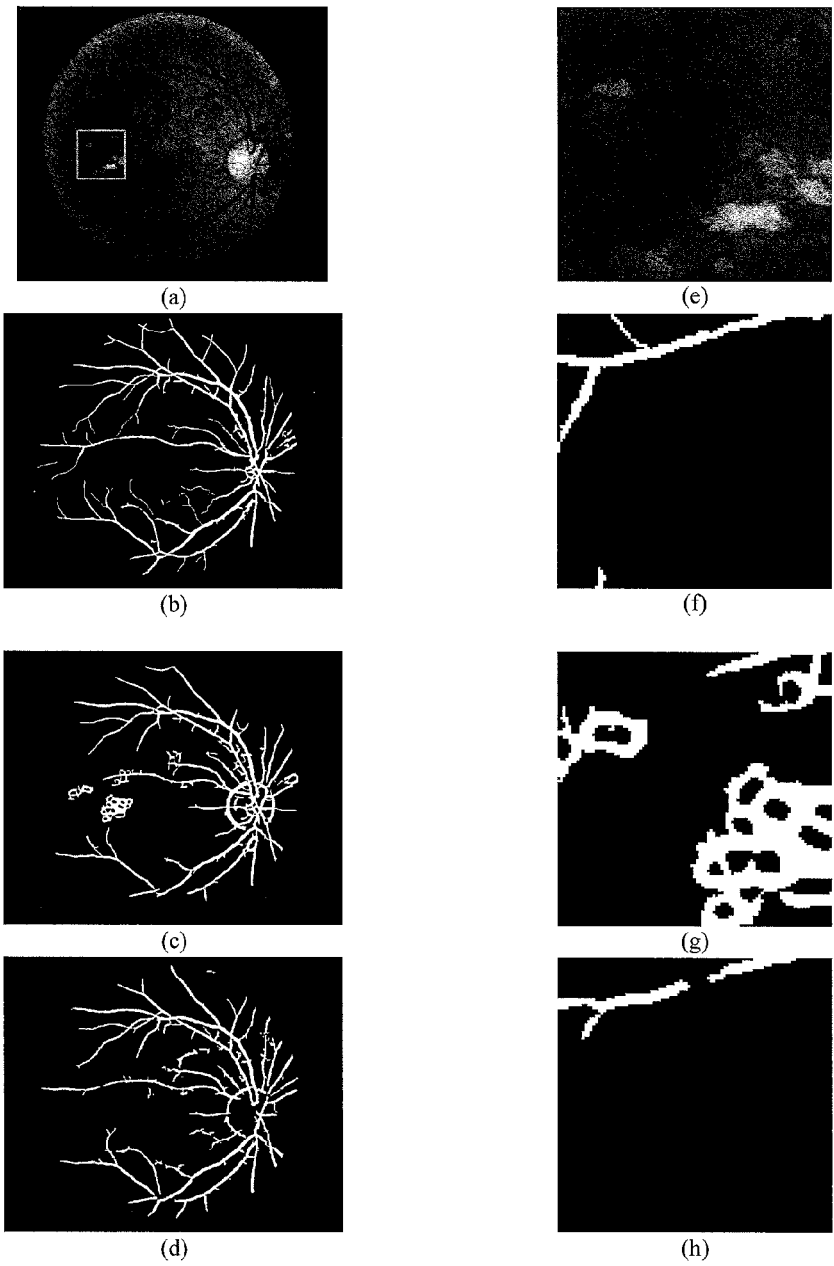
FIG. 26 shows (a) An original NPDR image in ZUEYE database; (b) hand-labeled ground truth; (c) the extracted vessel map by the scheme by Hoover [FPR=0.0373, TPR=0.7816; ACC=0.9449]; (d) the extracted vessel map by the method of the present invention [FPR=0.0320; TPR=0.7915; ACC=0.9506]; (e)~(h) are zoom-in images of (a)~(d).
Figure 27:
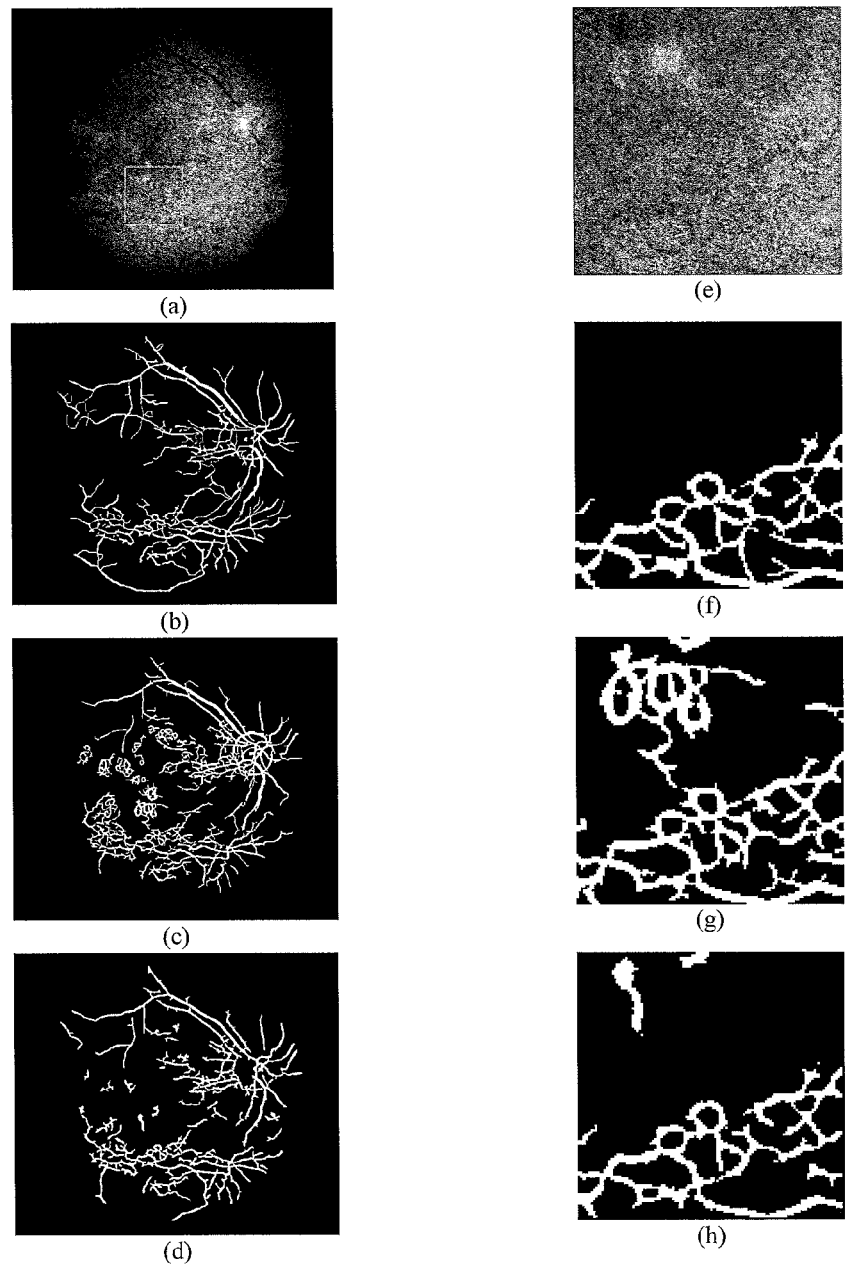
FIG. 27 shows (a) an original PDR image in ZUEYE database; (b) hand-labeled ground truth; (c) the extracted vessel map by the scheme by Hoover [FPR=0.0479, TPR=0.6754; ACC=0.9243]; (d) the extracted vessel map by the method of the present invention [FPR=0.0324, TPR=0.7959; ACC=0.9502]; (e)~(h) are zoom-in images of (a)~(d).

We evaluated the performance of proposed MMFDST scheme on screening PDR by applying it to the ZUEYE database, which consists of retinal images from DR patients. The color fundus images were captured by using Kowa VK-3 fundus camera at 45° field of view (FOV) and they were stored in 24-bits digital format. The resolution of the images is 800×608. There are 15 retinal images with DR in ZUEYE, including 10 NPDR and 5 PDR. FIGS. 26 and 27 present 2 examples of vessel extraction by applying the proposed method to one PDR and one NPDR retinal images in ZUEYE. The improved matched filter developed by Hoover is used for comparison. In the experiments, we set $\sigma_1=1$ to extract small vessels and $\sigma_2=1.7$ to extract large vessels. By varying the values of $T_h$, different true positive ratios and false positive ratios can be obtained. Table 3.4 lists the most accurate results obtained using the Hoover's method and our MMFDST.

FIG. 26 (a) shows an NPDR retinal image. FIG. 26 (b) is the hand-labeled ground truth of vessel map and FIGS. 26 (c) and (d) show the vessel maps extracted using respectively the Hoover's method and the proposed MMFDST method. We see that the proposed MMFDST method can eliminate most of the false detection of vessels caused by the strong edges of bright lesions. To make this easier to see, we have cropped and zoomed-in part of the images in FIG. 26 (e)~(h). FIG. 27 (a) shows a PDR retinal image, (b) is the hand-labeled ground truth of vessel map, (c)~(d) show the extracted vessel maps using the Hoover's method and the proposed method. We see that the proposed method can detect most of the neovasculars (new vessels) and eliminate most of the false detection of vessels caused by the strong edges of bright lesions. We crop and zoom-in part of the images and show them in FIG. 27 (e)~(h). It is seen that the false vessels caused by bright lesions (top left) in FIG. 27 (g) are reduced greatly in FIG. 27 (h) while the abnormal fine neovascular structures (bottom) being well detected.

Observing FIG. 26 (d) (NPDR case) and FIG. 27 (d) (PDR case), it is possible to distinguish PDR from NPDR because the PDR image tends to have more vessels in a local window and the neovasculars tend to have a large curvature. As shown in FIG. 27 (d), most of the neovasculars were extracted by our method and few false vessel detections were produced by our method. However, if we apply Hoover's method as shown at FIG. 26 (c), we can see that the edges of lesions could be misclassified as neovasculars because they have large local densities and large curvature.

Evaluation on the Public STARE Database

In this section, we tested the ability of the proposed MMFDST scheme to suppress lesions, comparing its performance with the performance of two state-of-the-art schemes, those of Hoover and Mendonca. The STARE database consists of retinal images captured by the TopCon TRV-50 fundus camera at 35° FOV, digitized at 24-bits with a spatial resolution of 700×605 pixels. In his report, Hoover selected 20 images for experiments, ten images of healthy ocular fundus and ten images of pathological fundus as ground truth, we used images hand-labeled by the first observer (labels-ah). We set $\sigma_1=1$ to extract small vessels and $\sigma_2=2$ to extract large vessels. The best averaging accuracies for normal images and pathological images are listed in Table 3.5.

Figure 28:
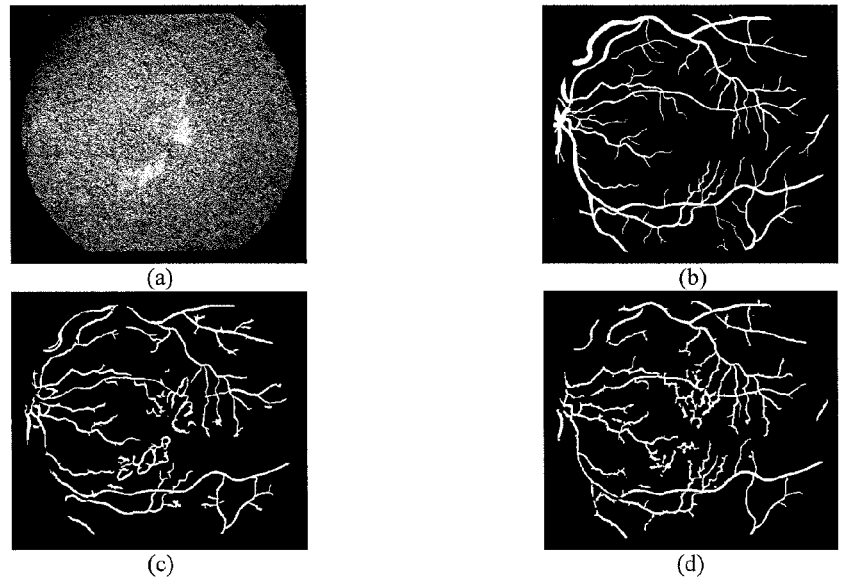
FIG. 28 shows (a) an pathological image in the STARE database; (b) the hand-labeled ground truth; (c) the extracted vessel map by a prior art scheme of Hoover [Accuracy=0.9198, TPR=0.5937, FPR=0.0402]; (d) the extracted vessel map by the method of the present invention [Accuracy=0.9302, TPR=0.6619, FPR=0.0368].

FIG. 28 (a) shows a pathological image from the STARE database, (b) shows the ground truth as manually labeled by the first observer (labels-ah), (c) shows an image of a vessel extracted using a previous known scheme and (d) shows the vessel map extracted using the method of the present invention, which not only detects more small vessels than methods proposed by Hoover and Mendonça and does so at a lower FPR, it also makes fewer false detections. These advantages are very important because the edges of bright lesions have large curvatures as shown at FIG. 28 (c) so it is easy to misclassify them as neovascular.

Figure 29:
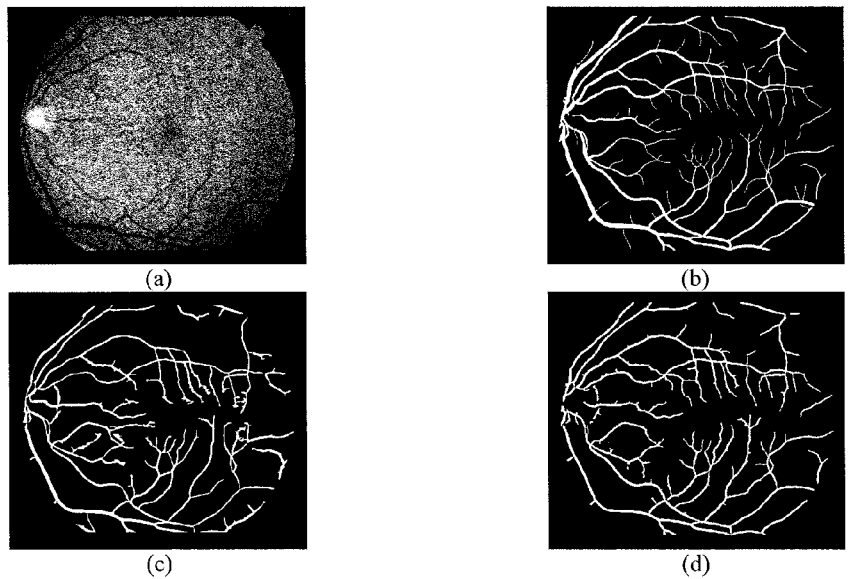
FIG. 29 shows (a) a normal image in the STARE database; (b) the hand-labeled ground truth; (c) the extracted vessel map by a prior art scheme of Hoover [Accuracy=0.9320, TPR=0.6992, FPR=0.0393]; (d) the extracted vessel map by the method of the present invention [Accuracy=0.9487, TPR=0.7625, FPR=0.0283].

FIG. 29 (a) shows a normal image from the STARE database, (b) shows the ground truth as manually labeled by the first observer (labels-ah), (c) shows an image of vessels extracted using the Hoover's method and (d) shows the vessel map extracted using the method of the present invention, which as shown can detect more small vessels than Hoover's method.

Table 3.5 lists the results of ACC, TPR and FPR for the STARE database extracted by different methods. Table 3.6 compares the running time of the proposed method with those state-of-art methods. From Tables 3.IV and 3.V, we can see that the proposed method gets the highest TPR on the pathological images at a very low FPR. It also has a much lower computational complexity than that of Hoover's method and Mendonca's method.

TABLE 3.4

Extraction Results of ZUEYE Database

| Method | Accuracy | TPR | FPR |
| --- | --- | --- | --- |
| Hoover [4] | 0.9380 | 0.7462 | 0.0408 |
| Proposed method | 0.9536 | 0.7954 | 0.0311 |

TABLE 3.5

Extraction Results of STARE Database

| Method | Accuracy | TPR | FPR |
|---|---|---|---|
| *Normal cases* | | | |
| 2nd Human observer | 0.9283 | 0.8252 | 0.0456 |
| Hoover [4] | 0.9324 | 0.6736 | 0.0528 |
| Mendonça [7] | 0.9531 | 0.7366 | 0.0178 |
| Proposed method | 0.9497 | 0.6611 | 0.0152 |
| *Pathological cases* | | | |
| 2nd Human observer | 0.9425 | 0.8252 | 0.0456 |
| Hoover [4] | 0.9211 | 0.6736 | 0.0528 |
| Mendonça [7] | 0.9426 | 0.6801 | 0.0306 |
| Proposed method | 0.9416 | 0.7286 | 0.0372 |

TABLE 3.6

Running Time per Image in STARE Database

| Method | System Environment | Running Time |
|---|---|---|
| Hoover [4] | P-III 1.5 GHz, 512 Mb RAM, Windows executable | 0.5 minute |
| Mendonça [7] | P-IV 3.2 GHz, 960 Mb RAM, Matlab | 3 minutes |
| Proposed method | P-III 1.5 GHz, 512 Mb RAM, Matlab | 0.5 minute |

Top-Down Retinal Image Segmentation System for Diabetic Retinopathy Screening

Despite many efforts have been made in the art, retinal image segmentation remains a difficult task. The major difficulty comes from the fact that retinal objects-pathological and physical-mutually affect each other, producing false positives for one feature or another. For example, the extraction of vessels may be affected by bright lesions and red lesions; the extraction of bright lesions may be affected by the optic disc; and the extraction of the optic disc may be affected by bright lesions and vessels.

Figure 30:
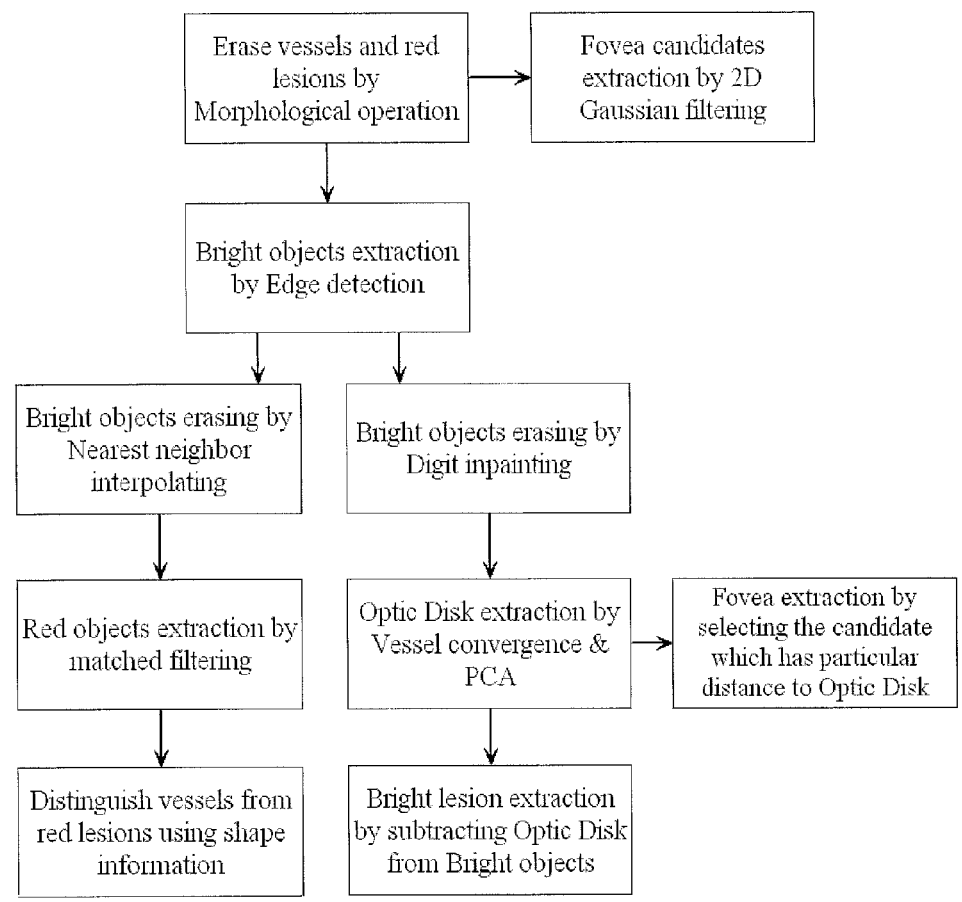
FIG. 30 is a diagram showing a scheme to segment retinal images for DR diagnosis according to the present invention.
Figure 31:
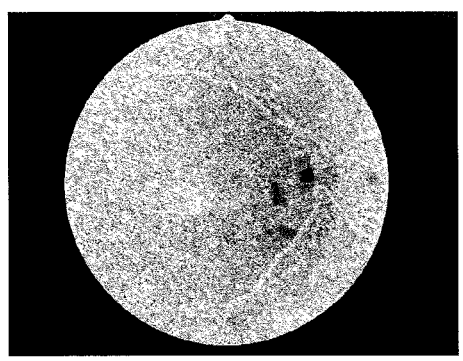
FIG. 31 shows a process of eliminating vessels. (a) the inversed green channel $\overline{I_g}$, (b) $I_1$: eroded (b), (c) $I_2$: reconstructed $I_1$, (d) $\overline{I_2}$: inversed $I_2$
Figure 31:
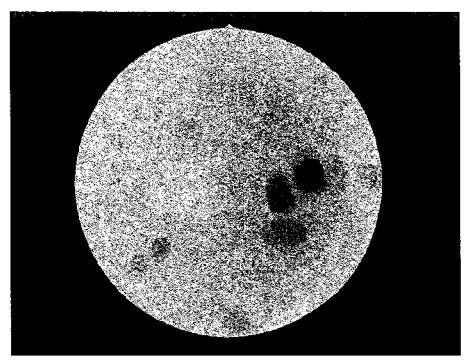
Figure 31:
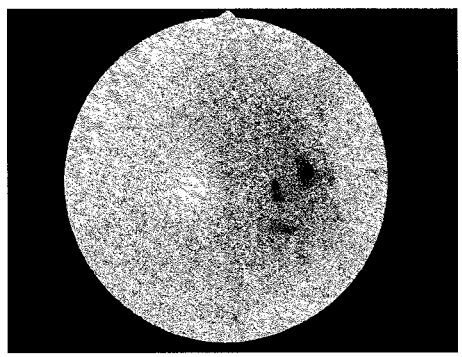
Figure 31:
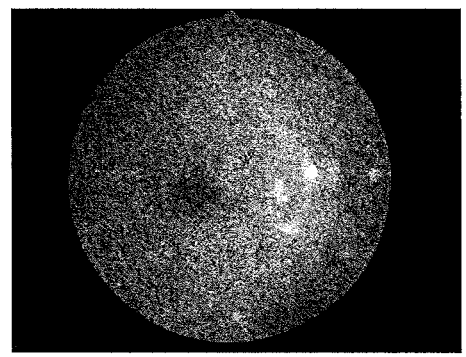

In the present invention, a Top-Down scheme to extract the features to diagnosis DR is developed. This scheme can suppress the affection among features during feature extraction. FIG. 30 shows the Top-Down Scheme of the present invention. As shown, the proposed scheme will segment all bright objects and red objects first. Then the bright objects will be classified into bright lesions and the optic disk. And the red objects will be classified into vessels and red lesions. Notice that in this Top-Down scheme the fovea is not defined as red objects simply because it is too large to be found by our "red objects finder". The fovea is finally located with the help of the location of the optic disk. The segmentation of bright objects will help the segmentation of vessels, and then the segmentation of vessels will help the segmentation of the optic disk, and then the segmentation of the optic disk will help the segmentation of the bright lesions and the fovea. Therefore the relations among different objects in retina have been efficiently used by our scheme.

Bright Object Segmentation

Retinal bright objects include bright lesions and the optic disc. As shown in FIG. 30, all bright objects is segmented first. Then the optic disc will be separated from bright lesions.

Finding all Bright Objects

Because the size and brightness of bright objects can vary a lot in a retinal image with DR, edge is the most robust feature to find all bright objects. The present invention improves the method proposed by Walter and is briefly described as follows:

Step 1): Eliminating vessels. Vessels produce strong edges. These strong edges must be eliminated before edge detection. As reported, Walter applied a morphological closing before the edge detection. But the closing operation will generate many disc-like structures, which means the image will be not as smooth as before. These disc-like structures may result in false detection of bright lesions.

The morphological "erode followed by reconstruction" operation will usually produce smoother results than closing. But it does not eliminate local minimum regions as well as closing.

The present invention proposes a controlled reconstruction here. First, the vessels are eliminated by erode defined by Equation 4.1:

$$I_1 = \overline{I_g} \ominus B_{S1} \qquad (4.1)$$

where $\overline{I_g}$ is the complement of the green channel of the original image, $\ominus$ is erode, $B_{S1}$ is a disc structure with radius S1 pixels. S1 should be large enough to eliminate all vessels. After that, with initializing $I_2=I_1$, the eroded image will be reconstructed by $$R = \min(I_2 \oplus B_1, \overline{I_g}); I_2 = R \qquad (4.2)$$

where $\oplus$ is dilate, $B_1$ is a disc structure with radius 1 pixel. The minimum of dilated $I_2$ image and $\overline{I_g}$ is assigned to R. Equation (4.2) will be repeated N times where N is larger than S1. FIG. 4.2 shows this step.

Step 2): Detecting edges. Once the vessels are eliminated, all edges remained on the image should be caused by bright lesions. We apply canny edge detector on $\overline{I_2}$ at two different scales and use scale multiplication to enhance the detection. The edge detection filter used here is FDOG.

$$f(x) = -x \cdot e^{-x^2/2} \qquad (4.3).$$

The dilation of f(x) by scale s is $$f(x) = -x \cdot e^{-x^2/2s^2}/s^2 \qquad (4.4).$$

A small scale $s_1$ and a large scale $s_2$ are used to detect edges. The responses of canny edge detector at two scales can be denoted as $R_{s_1}(x)$ and $R_{s_2}(x)$. The scale multiplication is defined as the product of $R_{s_1}(x)$ and $R_{s_2}(x)$ $$P(x) = R_{s_1}(x) \cdot R_{s_2}(x) \qquad (4.5).$$

Figure 32:
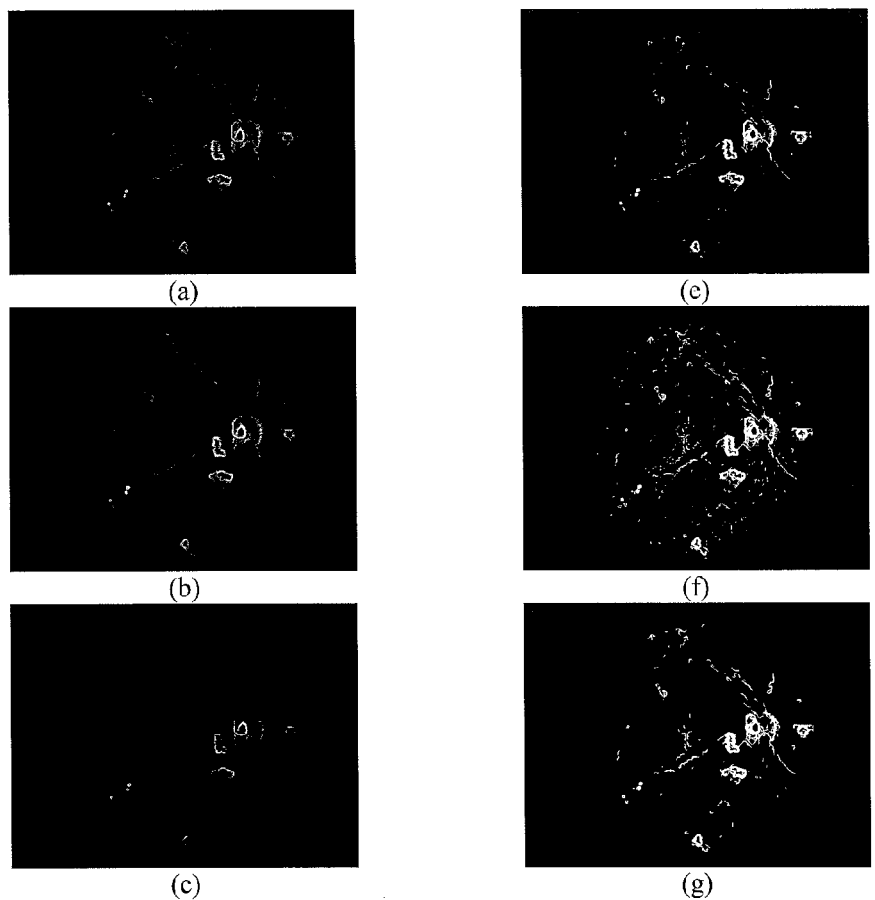
FIG. 32 shows a process of detecting edges. (a) and (b) canny edge detector at two different scales, (c) scale production of (a) and (b), (e) thresholding (c) with a high threshold, (f) thresholding (c) with a low threshold, (g) $I_3$: link (e) to (f).

The double thresholding strategy is used to threshold the canny filtering results. Double-thresholding imposes a low threshold $t_l$ and a high threshold $t_h = 2t_l$ are imposed on P(x), which produces two edge maps $E_l$ and $E_h$. The final edge map is formed by selecting edges in $E_l$ that link to the edges in $E_h$. This strategy is good at avoiding broken edges. FIG. 32 shows this step. FIG. 32(*a*)-(*c*) shows the effect of scale multiplication. The improvement from single scale to scale multiplication is obvious. FIG. 32 (*d*)-(*e*) shows the effect of double thresholding. The segmented result has few broken edges and many fewer false edges.

Figure 33:
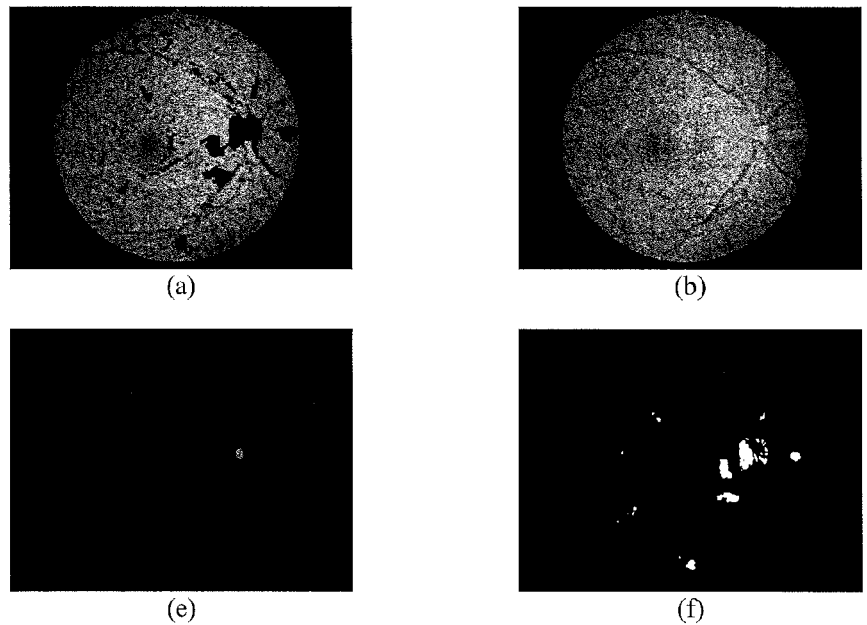
FIG. 33 shows a process of finding contour of bright lesions. (a) reconstruction marker, (b) reconstructed image $I_5$, (c) difference between $I_5$ and $I_g$, (d) thresholding.

Step 3): Finding the contours of bright objects. The method proposed by Walter is employed here to locate the final contour of the bright objects from a selection of bright object candidates. After filling of the holes in $I_3$, the filled objects will be regarded as bright object candidates. The exact contour of the bright lesions will be extracted by morphological reconstruction. The marker image $I_4$ is generated by setting all the candidates to 0 in the green channel of the original image $I_g$. The mask image is $I_g$. The difference between the reconstructed image $I_5$ and $I_g$ is double thresholded to generate the bright objects $I_6$. FIG. 33 shows this step.

Extracting the Optic Disc and Bright Lesions

Figure 34:
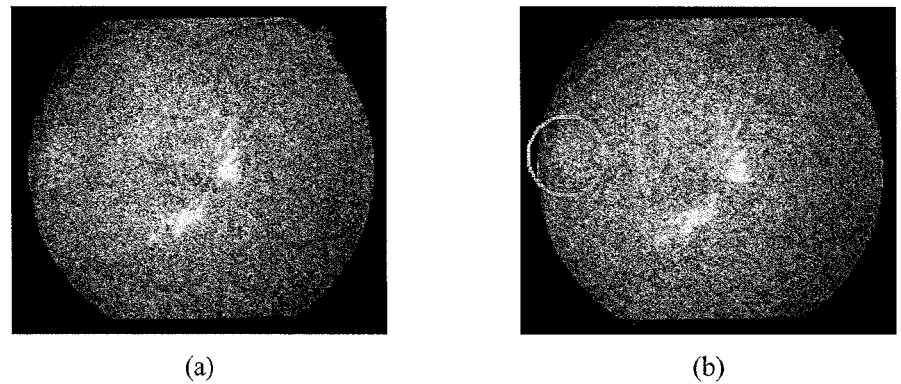
FIG. 34 shows the result of optic disc extraction. (a) by a PCA based method (b) by the method of the present invention.

After bright objects have been extracted, they have to be classified into bright lesions and the optic disc. To this end, we propose a method for extracting the optic disc, which provides better accuracy. A major difficulty in optic disc segmentation is from the bright lesions, which are easy to be recognized as optic discs. FIG. 34 shows an example using an image from the STARE database.

In FIG. 34 (a), the optic disc is located using a PCA based method. The methods are greatly affected by bright lesions. To find the correct vessel convergence, we first erase all bright objects and then improve accuracy by combining the vessel convergence based method and the PCA based method together. The details are as follows.

Step 1): Erasing bright objects by digit inpainting. To find the vessel convergence, it is first necessary to find the vessels. The matched filter can used to produce good vessel segmentation and avoid broken vessels. Because the optic disc must be at the convergence of large vessels, we use a matched filter with large to ignore small vessels. One problem of a matched filter is that it produces strong responses to the edges of bright objects. To avoid false positives of vessels, bright objects should be erased before applying a matched filter. A simple way to erase the bright objects is to pad the holes using morphological reconstruction as shown in FIG. 33 (a) & (b). But the edge of the area padded by this method is not smooth enough. We choose the exemplar-based inpainting which is known in the art to pad the holes.

Figure 35:
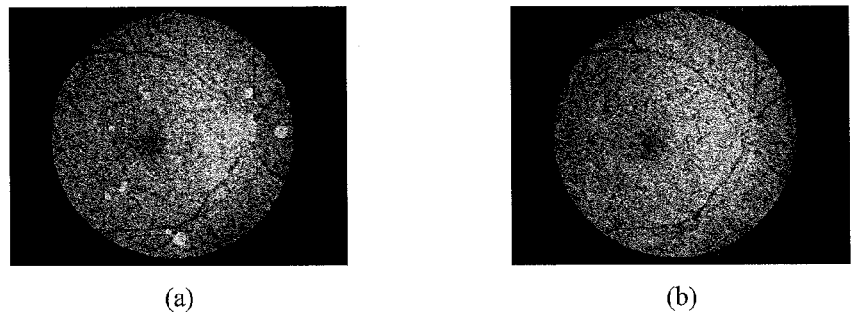
FIG. 35 shows the result of erasing bright objects. (a) The mask for inpainting, (b) inpainting result.

Inpainting depends upon a bright object being regarded as a single object, but a bright object that is split by vessels may be taken for background, so the first step in inpainting is to implement a closing. This morphological closing is applied on $I_6$ (image of bright objects) and a morphological eroding is then applied to the closed image to ensure that the area surrounding bright objects are regarded as background. The eroded image and the original image can be used to generate the inpainting mask as shown in FIG. 35 (a). Finally, the inpainting can be applied based on that inpainting mask to generate the image $I_7$ that has no bright objects.

FIG. 35 (b) shows the result of inpainting. The edges are very smooth, which means that vessel false positives can be better suppressed. One problem of this method, however, is that it will make the vessels which is crossing bright objects grow to wrong orientations. As shown in FIG. 35 (b), some vessels crossing the optic disc have been extended. The orientations estimated by inpainting are not the same as the original but they are sufficiently similar that it does not affect the identification of vessel convergence.

Figure 36:
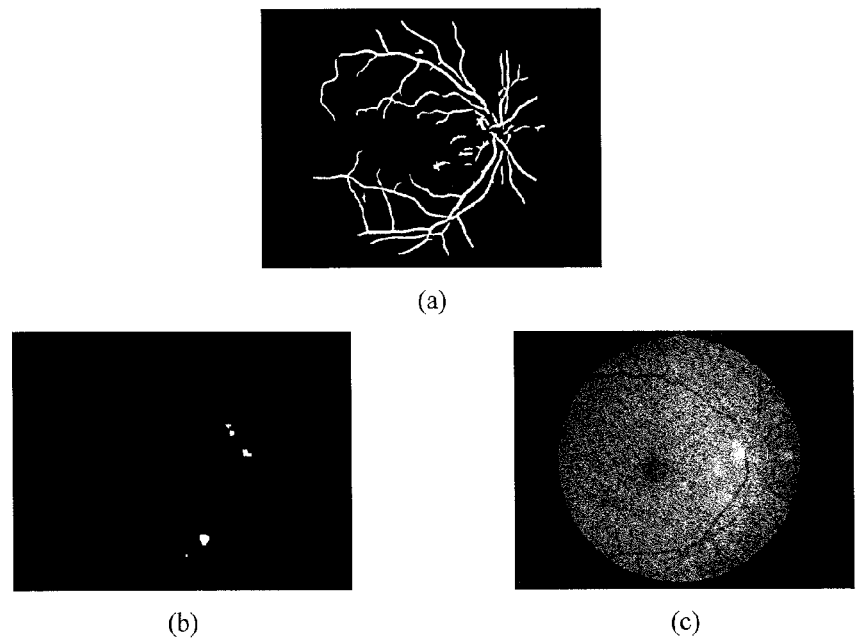
FIG. 36 shows the process of finding optic disc. (a) vessels, (b) regions of vessel convergence, (c) optic disc located.

Step 2): Finding vessel convergence. Large vessels and those with a high local contrast can be extracted by applying a matched filter with large σ (FIG. 36 (a)). Regions of vessel convergence can be located by applying a fuzzy convergence method. FIG. 36 (b) shows the vessel convergence. These regions of vessel convergence can be used as candidate optic disc.

Step 3): Locating optic discs. The centers of regions of vessel convergence are used as initial points where we apply the PCA based method. First, we manually cut some optic discs of the images to obtain the training data. We then calculate the eigen vectors of the covariance matrix of the training data, which we then refer to as eigen optic discs. We next iteratively move a square window on the retinal image using the initial points obtained above as the initial position of the iteration. The sub-image inside the square window is projected onto the optic disc space and the reconstruction error is calculated. The sub-image with the minimum reconstruction error will be classified as the optic disc. We denote the radius of an optic disc by $D_0$ so that the optic disc center is located at the initial point's N by N neighborhood, where N=2*$D_0$. FIG. 36 (c) shows the located optic disc. The opt is disc of average radius is indicated with a green circle.

Figure 37:
FIG. 37 shows bright lesions.

Step 4): Extracting bright lesions. Once the optic has been located, all bright objects outside the green circle shown in FIG. 36 (c) will be extracted as bright lesions which are shown in FIG. 37.

Red Object Segmentation

The retinal red objects include red lesions and vessels. There are kinds of red lesions. Here, as an example, we only focus on the segmentation of microaneurysm which is a major sign of DR and appear as small round objects. As shown in FIG. 30, first, the bright lesions will be erased to avoid false detections. Then the microaneurysms and vessels are separated using the mathematical morphology based method proposed by Spencer et al. and Frame et al. Finally, the microaneurysms are segmented based on the matched filter proposed by Spencer et al. and Frame et al. and the vessels are segmented based on the matched filter proposed by Chaudhuri et al. This procedure is further described as follows.

Figure 38:
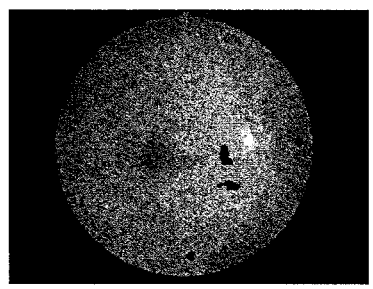
FIG. 38 shows (a) Image to pad; (b) Image padded; (c) $I_9$: image for red objects extraction.
Figure 38:
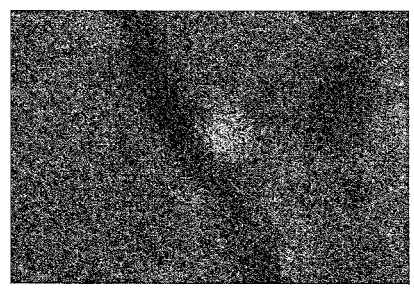
Figure 38:
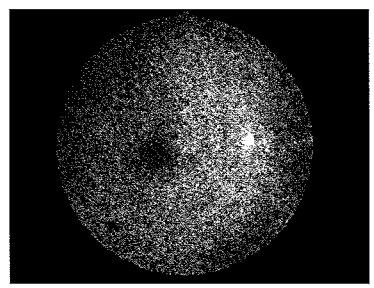
Figure 38:
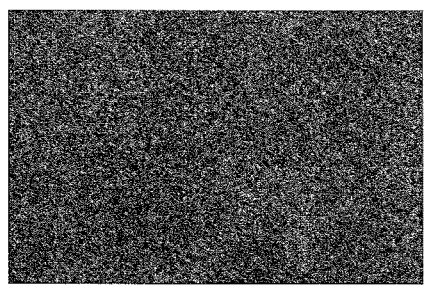
Figure 38:
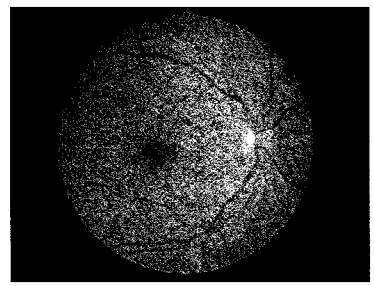
Figure 38:
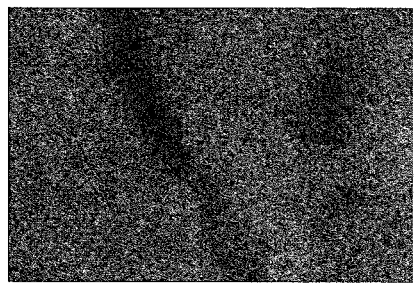

Step 1): Erasing bright objects by the nearest neighbor interpolation. Because bright objects will affect the detection of red objects, they should be erased before red object extraction. The bright objects were erased using exemplar based inpainting. The problem of this technique is that it makes the vessels which are crossing bright objects grow to wrong orientations. This will not affect the finding of vessel convergence, but will affect vessel extraction. To erase the bright objects, we use nearest neighbor interpolation for padding the area outside region of interest. First, the image to be padded is generated by imposing the image without vessels $\overline{I_2}$ (FIG. 32 (d)) on the bright lesion image $I_g$. The bright lesions are used as markers for padding. We erase all vessels here so that only background is used to pad the marked area. The optic disk has not been erased because the padding of the optic disk generally cause the lost of vessels inside it. Second, pixels which are inside the marked area and within the 4-neighborhood of the pixels outside the marked area are replaced with the mean value of their 8 neighbors outside the marked area. This procedure is repeated until the marked area is full. Third, the minimum of this padded image and $I_g$ (the green channel of the original image) is used to generate the image $I_9$ for following red object extraction. FIG. 38 (a) shows the padding markers; FIG. 38 (b) shows the padding result; FIG. 38 (c) shows $I_9$; FIGS. 38 (d), (e) and (f) are blocks of the $I_g$, padded result, and $I_9$, respectively.

Figure 39:
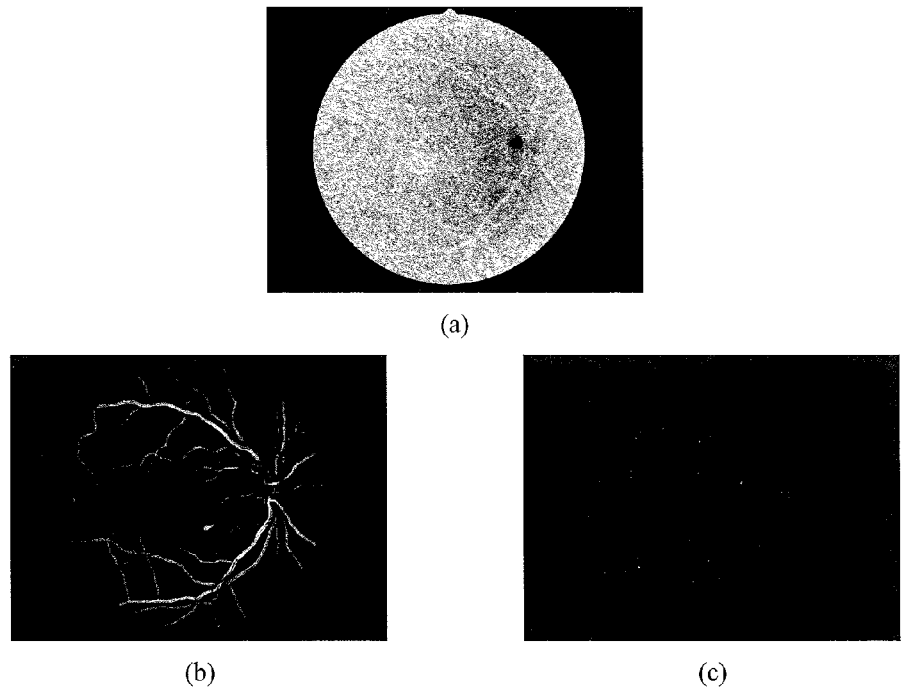
FIG. 39 shows (a) $\overline{I_9}$: implement of $I_9$; (b) $I_{vessel}$: image contains vessels; (c) $I_{ma}$: image contains microaneurysms.

Step 2): Microaneurysms and vessels separating. Spencer et al. and Frame et al. have proposed a modified morphological top-hat transformation to discriminate between circular, non-connected red lesions and the elongated vessels in FA (fluorescein angiographies) images. In order to use their modified top-hat transformation, $I_9$ has to be complemented first (shown at FIG. 39 (a), denoted as $\overline{I_9}$). A morphological opening with a linear structuring element at 12 different orientations is applied to $\overline{I_9}$. Using the maximum of the 12 opened images, we obtain an image $I_{vessel}$ which only contains vessels. We then subtract $I_{vessel}$ from $\overline{I_9}$ to obtain an image containing microaneurysms. FIG. 39 shows this step.

Figure 40:
FIG. 40 shows (a) enhanced vessels; (b) segmented vessels.

Step 3): Vessel extraction using MPMF. We segmented the vessels in the image $I_{vessel}$ by applying the MPMF as described in the foregoing. FIG. 40 shows this step.

Figure 41:
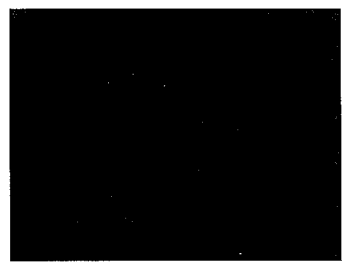
FIG. 41 shows (a) enhanced microaneurysms; (b) segmented microaneurysms.
Figure 41:
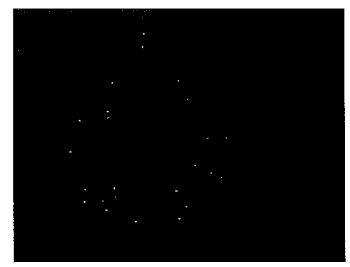

Step 4): Microaneurysm extraction based on the matched filter proposed by Spencer et al. and Frame et al. This matched filter is a 2-D Gaussian. Microaneurysms are enhanced and segmented as shown in FIG. 41.

Step 4): Microaneurysm extraction based on the matched filter proposed by Spencer et al. and Frame et al. This matched filter is a 2-D Gaussian. Microaneurysms are enhanced and segmented as shown in FIG. 41.

Figure 42:
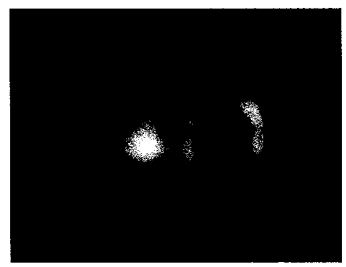
FIG. 42 show the result of finding fovea. (a) filter response, (b) fovea candidates, (c) fovea detected.
Figure 42:
Figure 42:
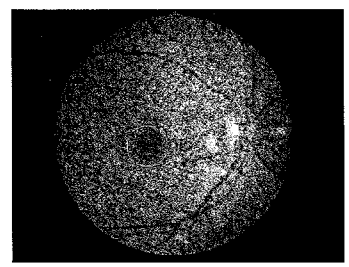

The filter response (FIG. 42 (a)) will be thresholded to identify the candidate regions as shown in FIG. 42 (b). We already have the location of the optic disk. The distance between the center of optic disk and fovea should be $4*D_0$. The candidate region which can satisfy this constraint will be regarded as the fovea. This constraint can further ensure the accuracy of fovea detection.

Experimental Results

We evaluated the performance of the proposed system by applying it to retinal images from DR patients. We used 20 images captured by using a Kowa VK-3 fundus camera at 45° field of view (FOV). The images were stored in 24-bit digital format. The resolution of the images is 800×608. We asked ophthalmologists to manually segment the images as the ground truth. All 20 images have microaneurysms and 15 images display bright lesions.

We evaluated the images in two ways, according to how many lesions were correctly classified and according to how many image pixels were correctly classified.

Pixel based evaluation was used to evaluate the performance of vessel segmentation and bright lesion segmentation. True positives (TP), that is, vessel pixels correctly classified, are defined as $$TP = \#[S(\delta^B(O_m) \wedge O_c)] \quad (4.7)$$

where # means "the number of", S(f) is the support of f, $\delta^B(f)$ means dilating f using structure element B, $\wedge$ is the logical "and" operation, $O_m$ are the manually segmented objects, and $O_c$ is the computerized segmentation. Here we set B as a disk of 1 pixel radius. We define false positives (FP), that is, background pixels classified as vessel pixels, and false negatives (FN), vessel pixels classified as background pixels, as $$FP = \#[S(O_c) \backslash S(\delta^B(O_m) \wedge O_c)] \quad (3.8)$$

$$FN = \#[(S(O_m) \backslash S(O_m \wedge \delta^B(O_c))] \quad (3.9)$$

where \ is the set difference. We plot sensitivity against predictive value to evaluate the performance. The structure element B used in our experiments is a disk of 1 pixel radius. With this dilation, some pixels on the edge of the targeted objects will be ignored in the evaluation. Those pixels are easy to be misclassified but are not important for clinicians. The performance measures are defined as $$\text{sensitivity} = \frac{TP}{TP + FN} = TPR \quad (3.10)$$

$$\text{specificity} = \frac{TN}{TN + FP} = TNR \quad (3.11)$$

$$\text{predictive value} = \frac{TP}{TP + FP} \quad (3.12)$$

Because all microaneurysms are of a similar size, we use lesion based evaluation to evaluate their extraction. The performance measures are the same with those defined above but do not apply the dilation operation.

Experiments on Bright Lesion Extraction

Figure 43:
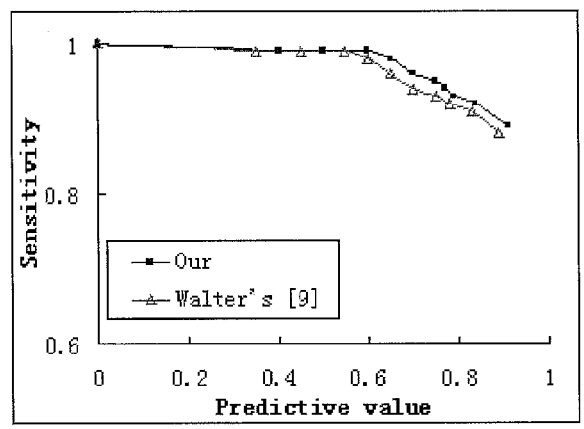
FIG. 43 shows bright lesion segmentation evaluation.

FIG. 43 shows the bright lesion extraction performance in terms of plot sensitivity against predictive value. While it is difficult to compare results on different databases, our method compared well with Walter and Sinthanayothin. We achieved a sensitivity of 89.5% and a predictive value 91.2% while the Walter's method achieved of sensitivity of 88.4% and a predictive value 89.3%. The results reported by Walter are a sensitivity of 92.8% and a predictive value of 92.4%. The results reported by Sinthanayothin are a sensitivity of 88.5% and a predictive value of 82.6%. The improvement in accuracy provided by the bright lesion extraction method of the present invention is satisfactory. We attribute it to improvements in controlled reconstruction, scale production, and double thresholding.

Experiments on Microaneurysm Extraction

Figure 44:
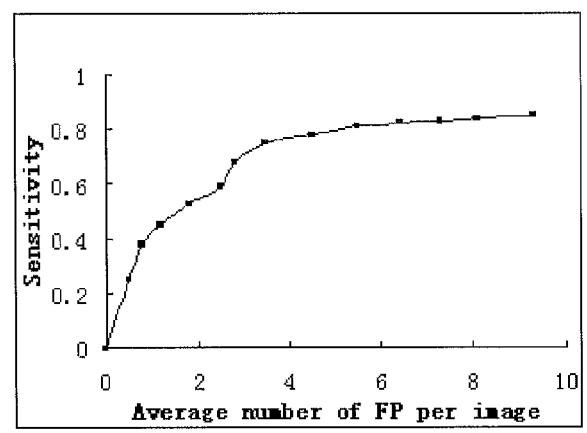
FIG. 44 shows microaneurysms extraction evaluation.

FIG. 44 shows the performance of our approach to microaneurysm extraction in terms of plot sensitivity against FP per image. Our microaneurysm extraction is, based on a simple method proposed by Frame and Spencer, which was actually designed for FA images. Again we compare the results of our method with that of Walter et al. Their method achieved a sensitivity of 88.47% at 2.13 FP per image. Our method achieves a sensitivity of 68.3% at 2.81 FP per image. While our method does not compare in terms of performance, it does show that a simple method normally used on FA images can be applied to color retinal images after appropriate preprocessing and can provide segmentation that is useful for clinicians. It also efficiently suppresses false positives.

Experiments on Vessel Extraction

Figure 45:
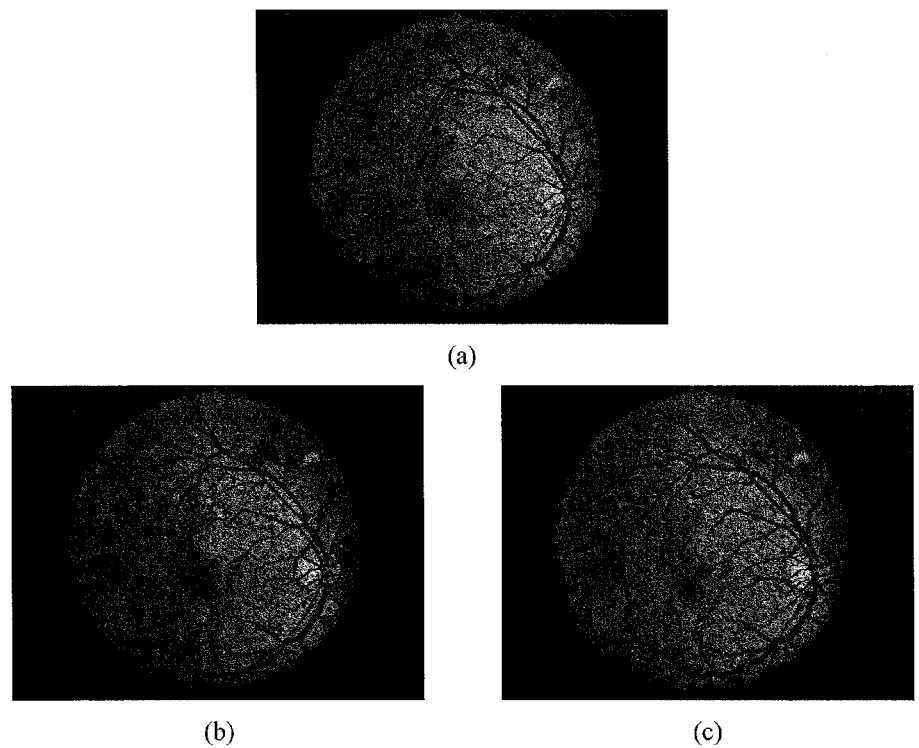
FIG. 45 shows an example of vessel extraction. (a) hand labeled ground truth; (b) Hoover's result [sensitivity=0.924, predictive value=0.846]; (c) the result of the present invention [sensitivity=0.937, predictive value=0.888].
Figure 46:
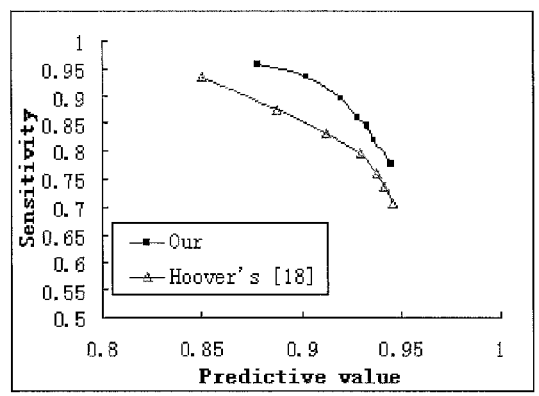
FIG. 46 shows vessel segmentation evaluation.

FIG. 45 shows an example of vessel extraction using our method. FIG. 46 shows the results for the extraction of red lesion in terms of plot sensitivity against predictive value comparing with Hoover's vessel extraction method. Because it has erased bright lesions, our method gets fewer false positives.

Experiments on Optic Disk

We evaluated the performance of the system of the present invention at detecting the optic disk using STARE database. To compare with the PCA based method proposed by Li and Chutatape, we implemented their algorithm. We used a leave-one-out scheme in which 19 images were used for training and one for testing. On STARE database, all 20 optic disks were accurately located by our method while 19 optic disks were accurately located by Li and Chutatape, which we attribute to the erasure of bright lesions preventing the false detections.

Experiments on Fovea

On our database, all 20 images present fovea clearly. On the experiment, all 20 foveae are accurately located because the correct location of optic disk provides a useful constraint for fovea detection.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A method of segmentation of a color retinal image for Diabetic Retinopathy (DR) diagnosis, the method comprising the steps of:
    (a) erasing edges of bright objects from a color retinal image by nearest neighbor interpolating, whereby an interpolated image is generated;
    (b) extracting vessel candidates from the interpolated image using multiscale production of matched filter;
    (c) eliminating non-vessels based on vessel texture feature measurement;

(d) erasing edges of bright objects from the color retinal image by fast digit inpainting whereby an inpainted image is generated; and (e) extracting an optic disk from the inpainted image; wherein the vessel texture feature measurement comprises applying spatial-statistical measurement for feature presentation.

2. The method according to claim 1, further comprising the steps of:

(f) extracting red objects by matched filtering, and (g) distinguishing the vessel candidates from red lesions using shape information.

3. The method according to claim 2, further comprising the steps of:

(h) extracting the optic disk by vessel convergence and principal component analysis (PCA), and (i) extracting bright lesions by subtracting the optic disk from the bright objects.

4. The method according to claim 3, further comprising the steps of:

(j) extracting fovea candidate regions having a particular distance to the optic disk; and (k) extracting the fovea candidate regions by 2D Gaussian filtering.

5. The method according to claim 2, further comprising the step of:

(h) classifying the red objects as red lesions or as vessels.

6. The method according to claim 2, wherein step (f) comprises extraction of microaneurysms.

7. The method according to claim 1, wherein the color retinal image is obtained using a color fundus camera.

8. The method according to claim 1, wherein the vessel candidates extracted comprise thin neovascular vessels.

9. The method according to claim 1, (b) simultaneously thin and wide vessel candidates are extracted.

10. The method according to claim 1, wherein DR is either Proliferative Diabetic Retinopathy (PDR) or Non-Proliferative Diabetic Retinopathy (NPDR).

11. The method according to claim 1, wherein step (b) is performed after enhancing the color retinal image.

12. The method according to claim 1, wherein the result of the nearest neighbor interpolating is used for red lesion extraction and wherein the result of the fast digit inpainting is used for optic disk extraction.

13. The method according to claim 1, further comprising the step of:

(f) classifying the bright objects as bright lesions or as optic disks.

* * * * *